(12) United States Patent
Tagawa et al.

(10) Patent No.: US 10,894,270 B2
(45) Date of Patent: Jan. 19, 2021

(54) LIQUID JET DISCHARGE DEVICE AND LIQUID JET DISCHARGE METHOD

(71) Applicant: National University Corporation Tokyo University of Agriculture and Technology, Fuchu (JP)

(72) Inventors: Yoshiyuki Tagawa, Fuchu (JP); Hajime Onuki, Fuchu (JP)

(73) Assignee: NATIONAL UNIVERSITY CORPORATION TOKYO UNIVERSITY OF AGRICULTURE AND TECHNOLOGY, Tokyo (JP)

(*) Notice: Subject to any disclaimer, the term of this patent is extended or adjusted under 35 U.S.C. 154(b) by 398 days.

(21) Appl. No.: 15/573,219

(22) PCT Filed: May 13, 2016

(86) PCT No.: PCT/JP2016/064392
§ 371 (c)(1),
(2) Date: Nov. 10, 2017

(87) PCT Pub. No.: WO2016/182081
PCT Pub. Date: Nov. 17, 2016

(65) Prior Publication Data
US 2018/0133745 A1    May 17, 2018

(30) Foreign Application Priority Data

May 14, 2015  (JP) .................................. 2015-099054
Aug. 25, 2015  (JP) .................................. 2015-166119

(51) Int. Cl.
B05C 5/02        (2006.01)
B41J 2/04        (2006.01)
(Continued)

(52) U.S. Cl.
CPC ................. *B05C 5/02* (2013.01); *A61M 5/30* (2013.01); *B01L 3/56* (2013.01); *B05C 5/00* (2013.01);
(Continued)

(58) Field of Classification Search
USPC ........................................................ 422/509
See application file for complete search history.

(56) References Cited

U.S. PATENT DOCUMENTS 4,029,473 A * 6/1977 Sharples ............... B01L 3/0293
                                                            422/509
2002/0116021 A1* 8/2002 Gordon .............. A61B 17/3203
                                                            606/167
(Continued)

FOREIGN PATENT DOCUMENTS

CN        1777452 A    5/2006
EP        1492586 B1   1/2009
(Continued)

OTHER PUBLICATIONS

International Search Report in PCT/JP2016/064392, dated Aug. 16, 2016, 3 pages.
(Continued)

*Primary Examiner* — Jill A Warden
*Assistant Examiner* — Brittany I Fisher
(74) *Attorney, Agent, or Firm* — Kilpatrick Townsend & Stockton LLP

(57) ABSTRACT

A liquid jet discharge device includes: a narrow tube having a tube shaped body that is open at both ends, and in which a discharge liquid being disposed therein, the discharge liquid contacting at least at an inner face of the narrow tube at a contact angle of less than 90 degrees; a container in which a transmission medium being disposed at a base side thereof where one end of the narrow tube is disposed, so as
(Continued)

to enable pressure to be transmitted to the discharge liquid; an adjustment mechanism that causes a liquid surface of the discharge liquid inside the narrow tube and an interface of the transmission medium outside the narrow tube and inside the container to be staggered in position along an axial direction of the narrow tube; and a generation mechanism that generates a pressure wave in the transmission medium such that a liquid jet is discharged from the discharge liquid inside the narrow tube.

15 Claims, 27 Drawing Sheets

(51) Int. Cl.
    *B41J 2/14*     (2006.01)
    *B05C 5/00*     (2006.01)
    *A61M 5/30*     (2006.01)
    *B01L 3/00*     (2006.01)

(52) U.S. Cl.
    CPC ............. *B41J 2/04* (2013.01); *B41J 2/14104* (2013.01); *B01L 2200/06* (2013.01); *B01L 2200/0636* (2013.01); *B01L 2400/0436* (2013.01); *B01L 2400/0487* (2013.01); *B01L 2400/0496* (2013.01); *B01L 2400/086* (2013.01); *B41J 2002/041* (2013.01)

(56) References Cited

U.S. PATENT DOCUMENTS

| | | | | |
|---|---|---|---|---|
| 2004/0260234 | A1* | 12/2004 | Srinivasan | A61M 5/30 604/66 |
| 2005/0154369 | A1* | 7/2005 | Broullette | A61M 5/3007 604/500 |
| 2006/0211132 | A1* | 9/2006 | Miledi | B01J 19/0046 436/180 |
| 2007/0086922 | A1* | 4/2007 | Andersson | G01N 35/1016 422/400 |
| 2008/0091139 | A1* | 4/2008 | Srinivasan | A61M 5/30 604/68 |
| 2013/0017148 | A1* | 1/2013 | Larsen | A61K 9/5094 424/1.11 |
| 2013/0066263 | A1 | 3/2013 | Yoh et al. | |
| 2013/0144207 | A1* | 6/2013 | Gonon | A61M 3/0216 604/70 |
| 2013/0153677 | A1* | 6/2013 | Leen | B05B 17/0615 239/102.1 |

FOREIGN PATENT DOCUMENTS

| | | |
|---|---|---|
| JP | 2006088090 A | 4/2006 |
| JP | 2006289971 A | 10/2006 |
| JP | 2010221182 A | 10/2010 |
| JP | 2013187365 A | 9/2013 |
| KR | 101424394 B1 | 7/2014 |
| WO | 2011/144496 A1 | 11/2011 |

OTHER PUBLICATIONS

Antkowiak et al, "Short-term Dynamics of a Density Interface Following an Impact," Journal of Fluid Mechanics, Cambridge University Press (CUP), 2007, 577, pp. 241-250. <hal-00126025>.

Kiyama et al., The Generation of a Liquid Jet Induced by a Pressue Impulse (Experimental Study on the Jet Velocity), Bulletim of the JSME, vol. 8-, No. 814, 2014, 1-12.

Onuki et al., "A Highly-Viscous Liquid Jet Generator," Japanese Journal of Multiphase Flow, Dec. 15, 2015, vol. 29, No. 4, pp. 335-342.

Onuki et al., "Generation System for High-Speed Focused-Shape Microjet/Microdroplet of Highly-Viscous Liquids," Chemical Engineering, Dec. 1, 2015, vol. 60, No. 12, pp. 37-41.

Onuki et al., "Generation System for Viscous Droplets and Supersonic Microjets," Journal of Japan Coating Technology Association, Dec. 30, 2015, vol. 50, No. 12, pp. 406-411.

Peters, et al.. "Highly focused supersonic microjets: numerical simulations." Journal of fluid mechanics 719 (2013): 587-605.

Tagawa et al., "Highly focused supersonic microjets." Physical review X 2, No. 3 (2012): 031002.

Extended European Search Report in EP16792805.0 dated May 4, 2018, 7 pages.

\* cited by examiner

LIQUID JET DISCHARGE DEVICE AND LIQUID JET DISCHARGE METHOD

TECHNICAL FIELD

The present invention relates to a liquid jet discharge device and a liquid jet discharge method.

BACKGROUND ART

Liquid jets have hitherto been utilized in various fields, such as ink jet printers (see, for example, "'Digital Printer Technology' Series: Ink Jet, published by Tokyo Denki University Publishing Department (2008), the Imaging Society of Japan, ISBN 978-4-501-62340-1 C3072 (referred to below as "Non-Patent Publication 1")), micromachined devices, and the like. The majority of such liquid jet discharge devices are devices that discharge liquid jets with a diameter of about the inner diameter of a discharge tube or greater. For example, piezo ink jet method and BUBBLE-JET® method employed in ink jet printers fall in this category, and are both methods that extrude a liquid from a discharge hole (nozzle). The diameter of discharged liquid droplets is thus the diameter of the discharge holes or greater.

In contrast thereto, when a large acceleration is imparted over a short period of time to a liquid surface of concave shape in a discharge tube, a liquid jet as thin as about ⅕ the inner diameter of the discharge tube may be discharged from the discharge tube. If such thin liquid jets may be applied, then the problem of blocking up, which is a problem in the extrusion methods of ink jet printers and the like, may be solved.

With regards to methods to generate such thin liquid jets, there is a method in which a laser is emitted onto a microtube filled with a liquid (see, for example, "Highly Focused Supersonic Microjets" by Y. Tagawa, N. Oudalov, C. W. Visser, I. R. Peters, D. van der Meer, C. Sun, A. Prosperetti, and D. Lohse, published in Physical Review X, Vol. 2, (2012), 031002 (referred to below as "Non-Patent Publication 2")).

Moreover, another generation method is to let a test tube filled with a liquid fall freely, and to use an impulse force generated by a collision with a floor (see, for example, "Short-Term Dynamics of a Density Interface Following an Impact" by A. Antkowiak, N. Bremond, S. L Dizes, and E. Villermaux, Journal of Fluid Mechanics, Vol. 577, (2007), pp. 241-250 (referred to below as "Non-Patent Publication 3"), and "The Generation of a Liquid Jet Induced by a Pressure Impulse" by A. Kiyama, Y. Noguchi, and Y. Tagawa published in Transactions of the Japan Society of Mechanical Engineers, Vol. 80, No. 814, 2014 (referred to below as "Non-Patent Publication 4")).

SUMMARY OF INVENTION

Technical Problem

The hitherto known liquid jets described above have low velocity increase ratios, about two times, for the discharged jet velocity with respect to the initial velocity, and it has been difficult to generate liquid jets using high viscosity liquids. Accordingly, there is demand for a microjet generation method having a high velocity increase ratio.

In consideration of the above circumstances, an object of the present disclosure is to provide a liquid jet discharge device having a high velocity increase ratio.

Solution to Problem

The present disclosure includes the following aspects.

[1] A liquid jet discharge device is provided that includes: a narrow tube having a tube shaped body that is open at both ends, and in which a discharge liquid being disposed therein, the discharge liquid contacting at least at an inner face of the narrow tube at a contact angle of less than 90 degrees; a container in which a transmission medium being disposed at a base side thereof where one end of the narrow tube is disposed, so as to enable pressure to be transmitted to the discharge liquid; an adjustment mechanism that causes a liquid surface of the discharge liquid inside the narrow tube and an interface of the transmission medium outside the narrow tube and inside the container to be staggered in position along an axial direction of the narrow tube; and a generation mechanism that generates a pressure wave in the transmission medium such that a liquid jet is discharged from the discharge liquid inside the narrow tube.

According to the liquid jet discharge device of [1], due to the contact angle of the discharge liquid against the inner face of the narrow tube being less than 90 degrees, the liquid surface of the discharge liquid inside the narrow tube forms a concave shape that dips toward the opposite side of the base side of the container. In this state, the generation mechanism generates a pressure wave in the transmission medium disposed outside the narrow tube so as to discharge the liquid jet from the discharge liquid inside the narrow tube. As a result, a pressure wave propagates from the transmission medium to the discharge liquid, flow is focused at the concave shaped liquid surface inside the narrow tube, and a long liquid jet thinner than the narrow tube is discharged from a central portion of the liquid surface.

When this occurs, the discharge velocity of the liquid jet may be adjusted by the adjustment mechanism staggering the positions of the liquid surface inside the narrow tube and the interface inside the container and outside the narrow tube (may be referred to below simply as the "interface outside the narrow tube") along the narrow tube axial direction. For example, by making the position of the liquid surface inside the narrow tube be more toward the base side of the container than the interface outside the narrow tube, the velocity of the liquid jet discharged from the narrow tube may be made a higher velocity than in cases in which the position of the liquid surface of the narrow tube is at the same position as the interface outside the narrow tube.

[2] The liquid jet discharge device of [1] is provided in which the transmission medium includes a transmission liquid that is disposed at least at an outside of the narrow tube and the base side inside the container; and a separator member that is disposed between the discharge liquid and the transmission liquid either inside the narrow tube or at an end portion of the narrow tube, so as to separate the transmission medium and the discharge liquid and to propagate a pressure wave from the transmission liquid to the discharge liquid.

According to the liquid jet discharge device of [2], the transmission medium is separated by the separator member into at least the transmission liquid disposed inside the container and outside the narrow tube, and the discharge liquid disposed inside the narrow tube, with the separator member capable of propagating a pressure wave. Thus, when the pressure wave is generated in the transmission liquid by the generation mechanism, the pressure wave propagates through the separator member to the discharge liquid, and the liquid jet is discharged from the liquid surface of the discharge liquid inside the narrow tube.

However, due to the discharge liquid and the transmission liquid being separated by the separator member, a different liquid than the discharge liquid may be employed as the transmission liquid. Namely, the usage amount of the discharge liquid may be reduced. Moreover, due to the transmission liquid, which is the transmission medium, being disposed inside the container and outside the narrow tube, it is easy to dispose the transmission medium (transmission liquid) inside the container.

[3] The liquid jet discharge device of [2] is provided in which the separator member is a membrane formed either inside the narrow tube or at the end portion of the narrow tube.

According to the liquid jet discharge device of [3], due to the membrane being formed either at an end portion of the narrow tube or inside the narrow tube, the pressure wave propagating from the transmission liquid may be efficiently propagated to the discharge liquid.

[4] The liquid jet discharge device of [2] is provided in which the separator member is a plug disposed inside the narrow tube so as to be capable of displacement, the plug having an acoustic impedance of from 1 time to 1.5 times the acoustic impedance of the discharge liquid.

According to the liquid jet discharge device of [4], the separator member is a plug formed inside the narrow tube, and due to the plug having an acoustic impedance of from 1 time to 1.5 times the acoustic impedance of the discharge liquid, the pressure wave propagating from the transmission liquid may be efficiently propagated to the discharge liquid.

[5] The liquid jet discharge device of [1] is provided in which the transmission medium is the discharge device.

According to the liquid jet discharge device of [5], since the transmission medium is the discharge liquid, the same discharge liquid may be disposed inside the container, both inside the narrow tube and outside the narrow tube. The liquid surface outside the narrow tube and the liquid surface inside the narrow tube are staggered in position along the narrow tube axial direction by the adjustment mechanism, and the generation mechanism is driven. Thereby, the pressure wave is generated in the discharge liquid outside the narrow tube, and propagates to the discharge liquid inside the narrow tube, enabling the liquid jet to be discharged from the liquid surface of the discharge liquid inside the narrow tube.

[6] The liquid jet discharge device of [1] is provided in which the transmission medium the transmission medium is a solid body having an acoustic impedance of from 1 time to 1.5 times the acoustic impedance of the discharge liquid.

According to the liquid jet discharge device of [6], the transmission medium is a solid body having an acoustic impedance of from 1 time to 1.5 times the acoustic impedance of the discharge liquid. Thus, the pressure wave may be suppressed from attenuating at the interface between the transmission medium and the discharge liquid, and the pressure wave propagates efficiently to the discharge liquid inside the narrow tube. As a result, the liquid jet is discharged from the liquid surface of the discharge liquid.

In cases in which the transmission medium is a solid body, due to the interface of the transmission medium not shifting, the liquid level difference between the interface outside the narrow tube and the liquid surface inside the narrow tube may be adjusted by using only the amount of the discharge liquid inside the narrow tube.

Moreover, due to the transmission medium outside the narrow tube being a solid body, the discharge direction in which the liquid jet is discharged from the narrow tube may be freely set, such as to downward.

[7] The liquid jet discharge device of [4] or [5] is provided in which the adjustment mechanism is a narrow tube internal liquid surface displacement mechanism that displaces the liquid surface of the discharge liquid inside the narrow tube along the axial direction of the narrow tube.

According to the liquid jet discharge device of [7], the liquid surface inside the narrow tube and the interface outside the narrow tube are moved in opposite directions to each other along the narrow tube axial direction by the liquid surface of the discharge liquid inside the narrow tube being moved along the narrow tube axial direction by the narrow tube internal liquid surface displacement mechanism. This enables the liquid surface inside the narrow tube and the interface outside the narrow tube to be easily staggered in position along the narrow tube axial direction.

[8] The liquid jet discharge device of [4] or [5] is provided in which the adjustment mechanism is a narrow tube external interface displacement mechanism that displaces the interface of the transmission medium outside the narrow tube and inside the container along the axial direction of the narrow tube.

According to the liquid jet discharge device of [8], the liquid surface inside the narrow tube and the interface outside the narrow tube are moved in opposite directions to each other along the narrow tube axial direction by the interface of the transmission medium inside the container and outside the narrow tube being moved along the narrow tube axial direction by the narrow tube internal liquid surface displacement mechanism. This enables the liquid surface inside the narrow tube and the interface outside the narrow tube to be easily staggered in position along the narrow tube axial direction.

[9] The liquid jet discharge device of [3] or [6] is provided in which the adjustment mechanism is a discharge liquid feed mechanism that feeds the discharge liquid to the inside of the narrow tube.

According to the liquid jet discharge device of [9], due to the interface of the transmission medium not moving, a liquid level difference may be freely set between the liquid surface inside the narrow tube and the interface outside the narrow tube by adjusting only the amount of discharge liquid fed to the inside of the narrow tube by the discharge liquid feed mechanism.

[10] The liquid jet discharge device of any one of [1] to [9] is provided in which the generation mechanism is an impulse force imparting mechanism that imparts an impulse force to the container at the container base side of the liquid surface of the discharge liquid inside the narrow tube.

According to the liquid jet discharge device of [10], the pressure wave may be propagated to the liquid inside the narrow tube so as to discharge the liquid jet by the impulse force imparting mechanism imparting an impulse force to the container at the container base side of the interface inside the narrow tube. Namely, the pressure wave may be propagated to the liquid inside the narrow tube with a simple configuration.

[11] The liquid jet discharge device of any one of [2] to [5], [7], [8], and [9] when depending from [3] is provided in which the generation mechanism is a laser emitting mechanism that emits a laser onto the transmission medium at the container base side of the liquid surface of the discharge liquid inside the narrow tube.

According to the liquid jet discharge device of [11], by emitting a laser from a laser emitting means onto the transmission medium, i.e., onto the transmission liquid or the discharge liquid outside the narrow tube, at the container base side of the interface inside the narrow tube, bubbles are generated in the transmission liquid or the discharge liquid outside the narrow tube, and the pressure wave arising due to the generation of these bubbles propagates to the discharge liquid inside the narrow tube. Namely, the pressure wave may be propagated to the discharge liquid inside the narrow tube with a simple configuration.

[12] The liquid jet discharge device of any one of [1] to [9] is provided in which the generation mechanism is an explosive mechanism that causes an explosion to act on the transmission medium at the container base side of the liquid surface of the discharge liquid inside the narrow tube.

According to the liquid jet discharge device of [12], a pressure wave is generated in the transmission medium by the explosive mechanism causing an explosion to act on the transmission medium at the container base side of the liquid surface inside the narrow tube, and the pressure wave propagates to the discharge liquid inside the narrow tube. Namely, the pressure wave may be propagated to the discharge liquid inside the narrow tube with a simple configuration.

[13] The liquid jet discharge device of any one of [1] to [9] is provided in which the generation mechanism is an ultrasonic wave imparting mechanism that causes an ultrasonic wave to act on the transmission medium at the container base side of the liquid surface of the discharge liquid inside the narrow tube.

According to the liquid jet discharge device of [13], a pressure wave is generated in the transmission medium by the ultrasonic wave imparting mechanism causing an ultrasonic wave act to on the transmission medium at the container base side of the liquid surface inside the narrow tube, and the pressure wave propagates to the discharge liquid inside the narrow tube. Namely, the pressure wave may be propagated to the discharge liquid inside the narrow tube with a simple configuration.

[14] A liquid jet discharge method is provided including: a first process of disposing a transmission medium at a base side of a container, and disposing a discharge liquid inside a narrow tune so as to enable pressure transmission from the transmission medium, the narrow tube being open at both ends and disposed such that one end thereof is inserted into the transmission medium of the container and the other end thereof is disposed outside the transmission medium, the discharge liquid contacting at least at an inner face of the narrow tube at a contact angle of less than 90 degrees; and a second process of generating a pressure wave in the transmission medium inside the narrow tube so as to discharge a liquid jet from the discharge liquid inside the narrow tube, in a state in which a liquid surface of the discharge liquid inside the narrow tube and an interface of the transmission medium outside the narrow tube and inside the container are staggered in position along an axial direction of the narrow tube.

According to the liquid jet discharge method of [14], due to the contact angle of the discharge liquid against the inner face of the narrow tube being less than 90 degrees, the liquid surface of the discharge liquid inside the narrow tube forms a concave shape that dips toward the opposite side to the base side of the container.

In a state in which the liquid surface of the discharge liquid inside the narrow tube and the interface of the transmission medium outside the narrow tube and inside the container have been staggered in position along the narrow tube axial direction, the generation mechanism generates a pressure wave in the transmission medium disposed inside the container and outside the narrow tube.

As a result, a pressure wave propagates from the transmission medium to the discharge liquid, flow is focused at the concave shaped liquid surface inside the narrow tube, and a long liquid jet thinner than the narrow tube is discharged from a central portion of the liquid surface.

The discharge velocity of the liquid jet may be adjusted by staggering the positions of the liquid surface inside the narrow tube and the interface inside the container and outside the narrow tube along the narrow tube axial direction. For example, by making the position of the liquid surface inside the narrow tube be more toward the base side of the container than the interface outside the narrow tube, the velocity of the liquid jet discharged from the narrow tube may be made a higher velocity than in cases in which the position of the liquid surface of the narrow tube is at the same position as the interface outside the narrow tube.

DESCRIPTION OF EMBODIMENTS

Figure 1:
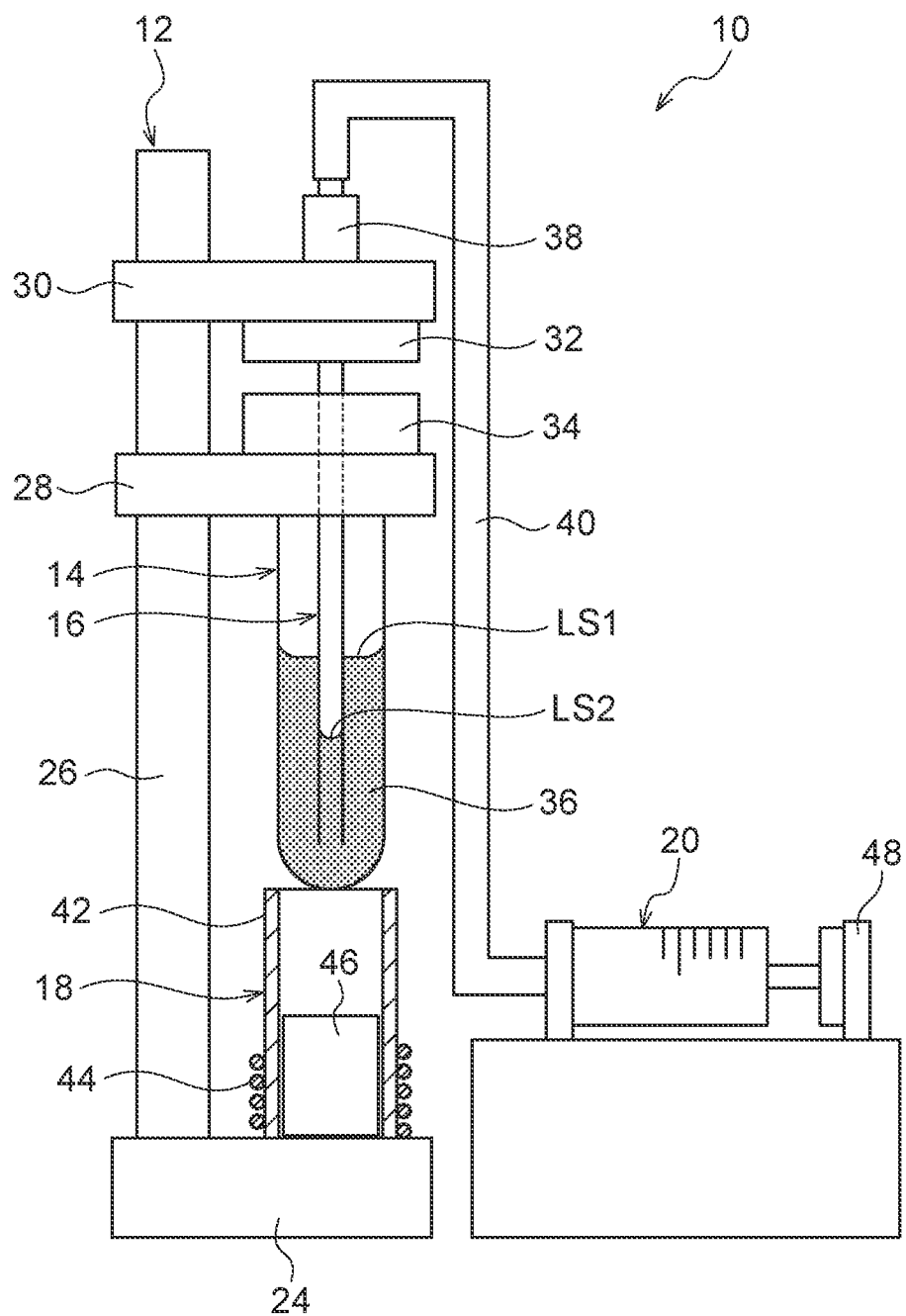
FIG. 1 is a schematic configuration diagram of a liquid jet discharge device according to a first exemplary embodiment.

A detailed explanation of exemplary embodiments of the present invention follows, with reference to the drawings.

First Exemplary Embodiment

Device Configuration

A liquid jet discharge device 10 according to a first exemplary embodiment of the present invention will first be described, with reference to FIG. 1. The liquid jet discharge device 10 includes a stand 12, a test tube 14 supported by the stand 12, a narrow tube 16 disposed inside the test tube 14, a coilgun 18 to impart impulse force to the test tube 14, and a syringe pump 20 to increase/reduce the barometric pressure inside the narrow tube 16.

In the present exemplary embodiment, the test tube 14 corresponds to a container of the present disclosure, the coilgun 18 corresponds to an impulse force imparting mechanism serving as a generation mechanism of the present disclosure, and the syringe pump 20 corresponds to an adjustment mechanism of the present disclosure.

The stand 12 includes a mounting base 24, a support bar 26 extending upright from the mounting base 24, a support ring 28 that is fixed to the support bar 26 and that supports the test tube 14 such that the test tube 14 is able to move upward, and a support ring 30 that is fixed to the support bar 26 above the support ring 28 and that supports the narrow tube 16 such that the narrow tube 16 is able to move upward. A shock absorber 32 is attached to a lower portion of the support ring 30 in order to avoid a situation in which the test tube 14 breaks due to the test tube 14 rising under an impulse force, described later, and colliding with the support ring 30.

The top end of the test tube 14 is hermetically sealed by a cap 34, and a liquid (silicone oil) 36 is placed inside the test tube 14. The test tube 14 is supported by the stand 12 by the cap 34 being placed on the support ring 28, such that the test tube 14 is able to move upward.

The narrow tube 16 is a tube that is narrower than the test tube 14, and that is open at both its top end and its bottom end. The narrow tube 16 is formed, for example, from a glass tube with good wettability (in which a contact angle of the liquid 36 is less than 90 degrees). The narrow tube 16 is gripped at its top end side by a clamp 38. The narrow tube 16 is supported by the stand 12 by the clamp 38 being placed on the support ring 30, such that the narrow tube 16 is able to move upward. The narrow tube 16 supported by the stand 12 has a bottom end that penetrates the cap 34 and reaches as far as the vicinity of the base of the test tube 14. As a result, the bottom end of the narrow tube 16 is inserted into the liquid 36 of the test tube 14, and the top end of the narrow tube 16 is positioned above the liquid 36. A connection tube 40 in communication with the syringe pump 20 is connected to the top end of the narrow tube 16. Note that the connection tube 40 may be flexible.

The coilgun 18 is disposed on the mounting base 24 of the stand 12. The coilgun 18 includes a cylindrical tube 42 placed on the mounting base, a coil 44 wound around the outer periphery of the bottom end of the cylindrical tube 42, and a metal rod 46 housed inside the cylindrical tube 42 so as to be capable of moving up and down. The metal rod 46 is formed in a circular pillar shape made from a steel material (JIS SS400). The cylindrical tube 42 extends from the mounting base 24 to the bottom end of the test tube 14. Thus, when the metal rod 46 is fired upward by passing current through the coil 44, the metal rod 46 collides with a base portion of the test tube 14.

The syringe pump 20 is driven such that in the test tube 14, described later, a liquid surface LS1 outside the narrow tube 16 (may be referred to below as "liquid surface LS1 outside the narrow tube 16") and a liquid surface LS2 inside the narrow tube 16 have a predetermined first liquid level difference $l_u$.

In the present exemplary embodiment, the liquid 36 inside the narrow tube 16 corresponds to the discharge liquid of the present disclosure, and the liquid 36 inside the test tube 14 and outside the narrow tube 16 corresponds to a transmission medium (transmission liquid) of the present disclosure.

In other words, in the present exemplary embodiment, the liquid 36 may correspond to both the discharge liquid and transmission medium (transmission liquid) of the present disclosure.

Operation

The operation of the liquid jet discharge device 10 configured as described above will now be described.

First, after the liquid 36 has been disposed in the test tube 14 and at the base portion side of the narrow tube 16, the syringe pump 20 is then driven such that a gas portion inside the narrow tube 16 is pressurized to a predetermined pressure. As a result, the pressure of the gas portion inside the narrow tube 16 is increased to a pressure higher than a gas portion outside the narrow tube 16 in the test tube 14, and the liquid surface LS2 inside the narrow tube 16 becomes lower than the liquid surface LS1 outside the narrow tube 16 (see FIG. 3A).

Figure 3A:
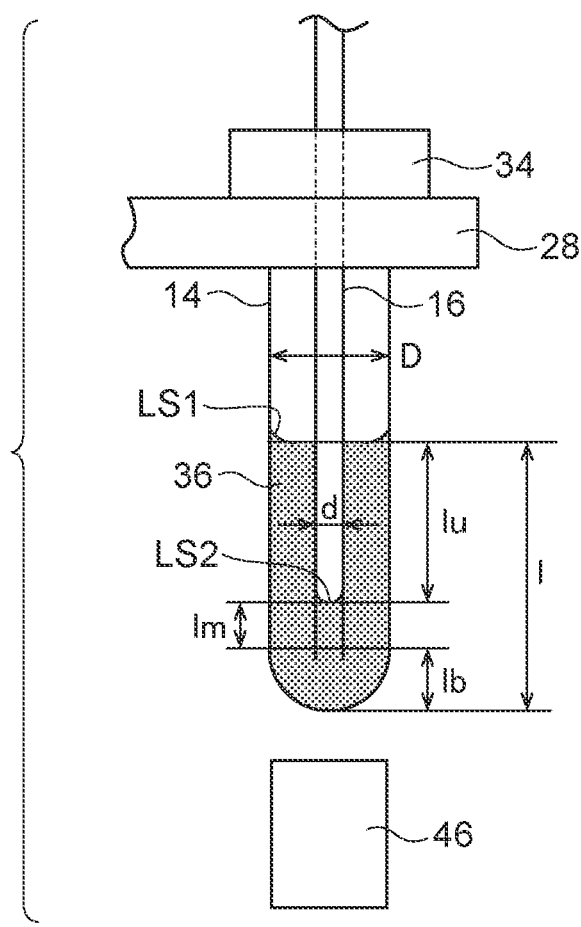
FIG. 3A is a schematic diagram to explain a state of a liquid surface prior to collision of a metal rod in a liquid jet discharge device according to the first exemplary embodiment.
Figure 3B:
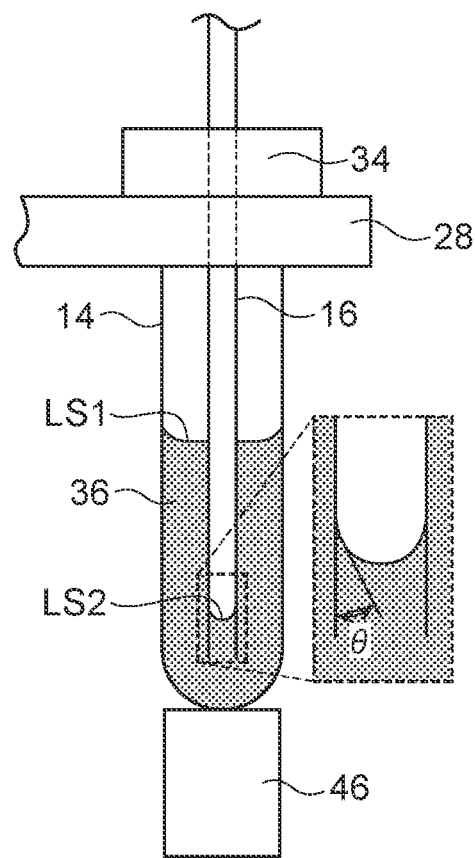
FIG. 3B is a schematic diagram to explain a state of a liquid surface during collision of a metal rod in the liquid jet discharge device according to the first exemplary embodiment.
Figure 3C:
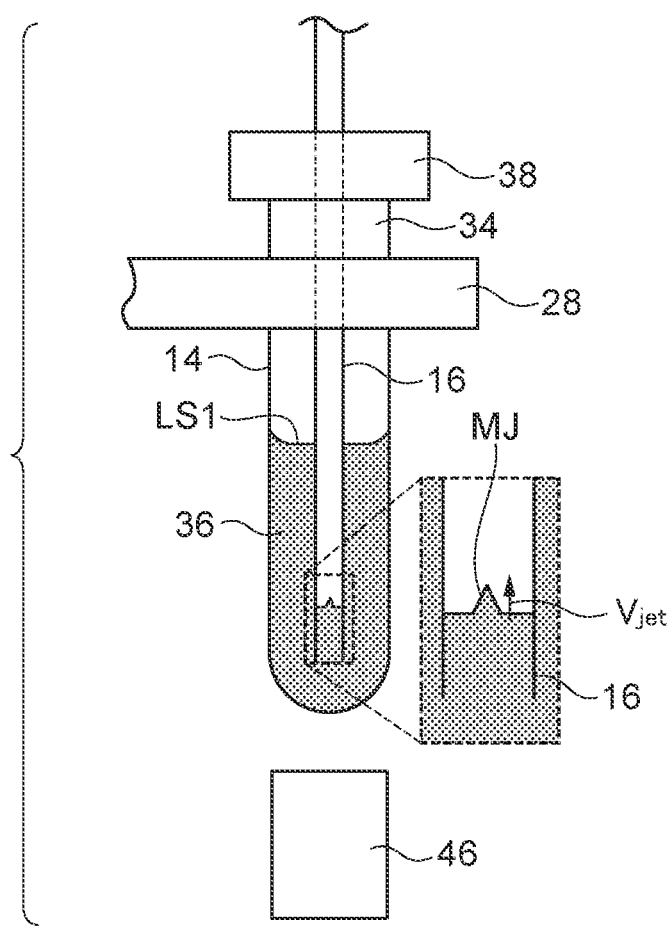
FIG. 3C is a schematic diagram to explain a state of a liquid surface after collision of a metal rod in the liquid jet discharge device according to the first exemplary embodiment.

From this state, the metal rod 46 inside the cylindrical tube 42 is then shot upward by electromagnetic induction by passing current through the coil 44 of the coilgun 18, and the metal rod 46 collides with the base of the test tube 14 (see FIG. 3B). The test tube 14 positioned above the cylindrical tube 42 jumps up due to the impulse force (see FIG. 3C). When this occurs, inside the narrow tube 16, the liquid surface LS2, which is formed as a concave surface due to the contact angle of the liquid 36 being less than 90 degrees, becomes a horizontal flat surface shape, and a liquid jet MJ narrower than the narrow tube 16 is ejected (discharged) from a central portion of the liquid surface LS2.

Figure 17A:
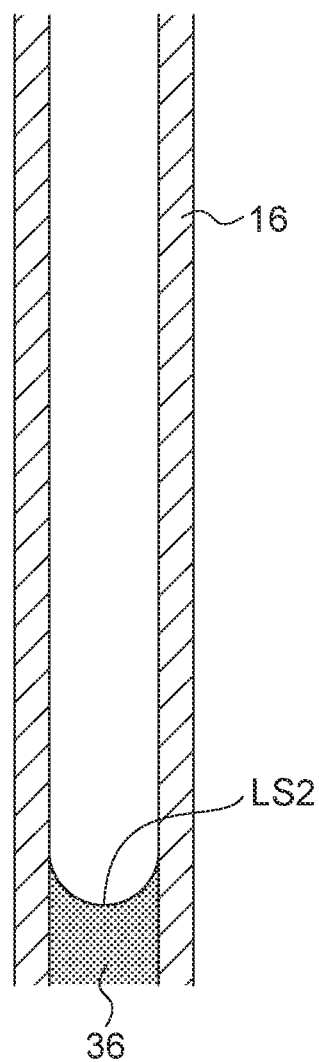
FIG. 17A is a diagram illustrating a state of a liquid surface inside the narrow tube in the liquid jet discharge device according to the first exemplary embodiment, prior to discharge.
Figure 17B:
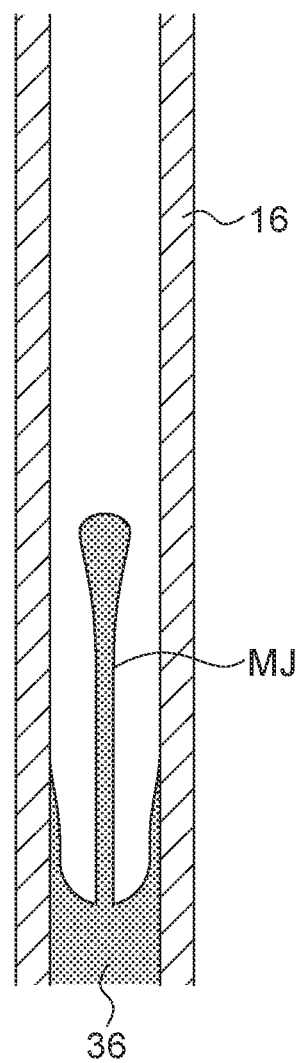
FIG. 17B is a diagram illustrating a state of the liquid surface inside the narrow tube in the liquid jet discharge device according to the first exemplary embodiment, immediately after discharge.
Figure 17C:
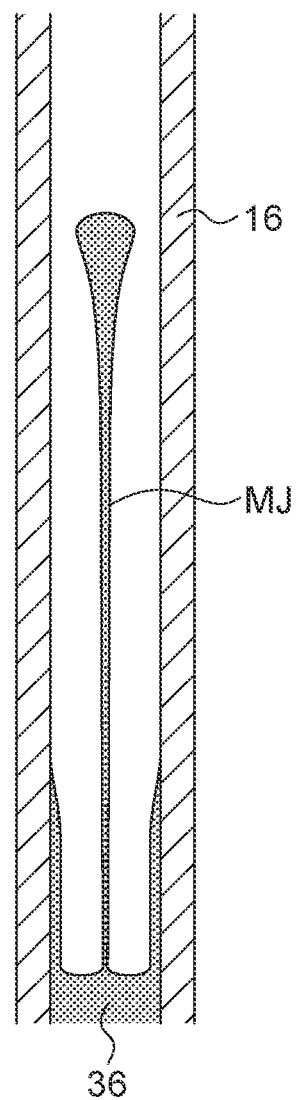
FIG. 17C is a diagram illustrating a state of the liquid surface inside the narrow tube in the liquid jet discharge device according to the first exemplary embodiment, when a small amount of time has elapsed from immediately after discharge.

Namely, as illustrated in FIG. 17A to FIG. 17C, the liquid jet MJ is discharged from a central portion of the liquid surface LS2 of the liquid 36 that is formed with a concave surface inside the narrow tube 16. The liquid jet MJ is narrower than the inner diameter of the narrow tube 16, and for example, is as narrow as about ⅕ the inner diameter of the narrow tube 16, and includes a leading end portion having a spherical bulge shape. Due to this discharge, the liquid surface LS2 is lowered downward, while the discharged liquid jet MJ extends even further.

In this manner, the "liquid jet MJ" described in a series of exemplary embodiments is a liquid jet discharged from the liquid surface LS2 with a focused, long, thin shape that is sufficiently thinner than the liquid surface LS2 (i.e., the inner diameter of the narrow tube 16). Note that the liquid jet MJ may be in a long, thin shape on arrival at a discharge receiving body, or may be in a state in which a droplet has been separated from the leading end portion thereof.

The liquid jet MJ has a large velocity increase ratio β (=$V_{jet}/U_0$) of jet velocity $V_{jet}$, described later, with respect to an initial velocity $U_0$, also described later.

Thus, a high proportion of energy from a fixed amount of energy imparted to the liquid 36 may be concentrated in the liquid jet MJ by discharging the liquid jet MJ with a high velocity increase ratio β (i.e., enabling the liquid jet MJ to be discharged extremely fast). This enables even high viscosity liquids 36, which hitherto have not been possible to discharge as a liquid jet, to be discharged in cases in which a fixed amount of energy is imparted to the liquid 36 of the liquid jet discharge device 10.

Parameters

Parameters that are employed to explain an analysis model to analyze the liquid jet MJ discharged by the liquid jet discharge device 10, and test results thereof, will be described below.

An analysis model according to an Example is an analysis model of a case in which a liquid jet MJ is discharged using the liquid jet discharge device 10. An analysis model according to a Comparative Example is an analysis model of a case in which a liquid jet MJ is discharged from a test tube 14 while removing the narrow tube 16 from the liquid jet discharge device 10.

Figure 4A:
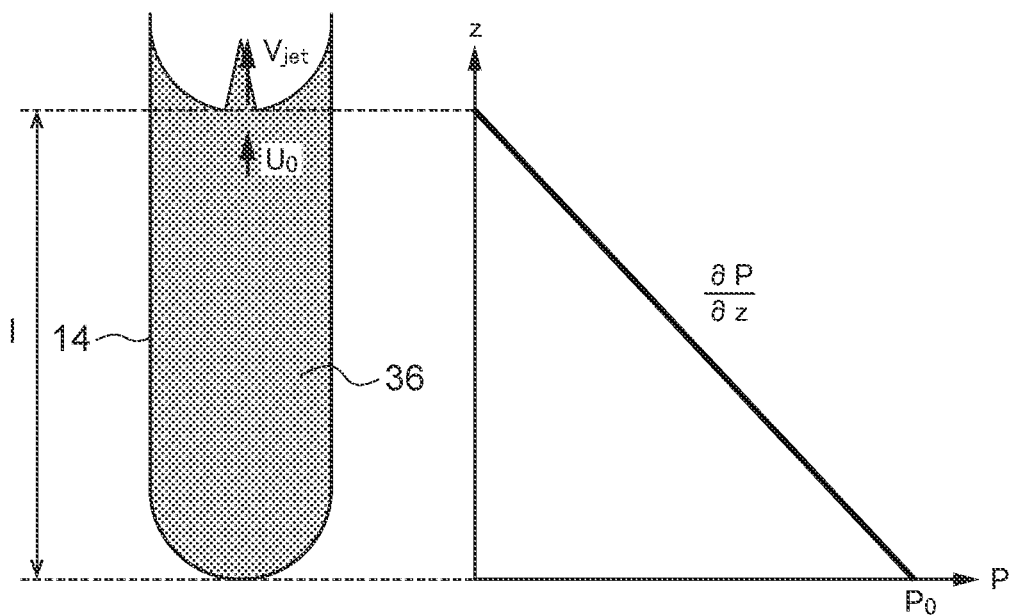
FIG. 4A is a schematic diagram of discharge of a microjet in a device according to a Comparative Example only equipped with a test tube, and a pressure impulse gradient thereof.

The parameters are as set out below (see FIG. 3A, FIG. 4A, and FIG. 4B).

l: a distance (liquid surface height, in mm) between a basal face (apex of a semi-spherical shape) of the test tube 14 and the liquid surface LS1 outside the narrow tube 16.

$l_u$: a distance (first liquid level difference, in mm) between the liquid surface LS2 inside the narrow tube 16 and the liquid surface LS1 outside the narrow tube 16 (wherein this distance is positive when the liquid surface LS2 inside the narrow tube 16 is lower (i.e., at the base side of the test tube 14).

$l_m$: a distance (second liquid level difference, in mm) between a bottom end face of the narrow tube 16 and the liquid surface LS2 inside the narrow tube 16.

$l_b$: a distance (third liquid level difference, in mm) between the basal face (apex of a semi-spherical shape) of the test tube 14 and the bottom end face of the narrow tube 16.

D: inner diameter of the test tube 14 (in mm).

d: inner diameter of the narrow tube 16 (in mm).

v: kinematic viscosity of the liquid 36 (in mm²/s) (may be referred to below simply as "viscosity").

Analysis Model

First, a physical model related to the jet velocity $V_{jet}$ of the liquid jet MJ generated by the liquid jet discharge device 10 will be described. As illustrated in FIG. 4A, consider a relationship between the initial velocity $U_0$ (of the test tube 14) imparted to the liquid 36 inside the test tube 14 and the jet velocity $V_{jet}$ in cases in which no narrow tube has been inserted into the test tube 14.

In cases in which the liquid 36 is suddenly accelerated by impulse force, the velocity of the liquid 36 during the sudden change, and the velocity at the boundary with the test tube 14 in the vicinity of the tube wall, are not large. Thus, terms in Navier-Stokes equations that only include velocity and spatial differentials may be ignored since they are much smaller compared to other terms. Doing so, from the Navier-Stokes equations give an initial velocity $U_0$ imparted to a liquid 36 as below, wherein ρ is density:

$$U_0 = -\frac{1}{\rho}\frac{\partial P}{\partial z} \quad (1)$$

Wherein P is the pressure impulse and is expressed by the following equation with pressure p, and time the impulse force continues for τ.

$$P = \int_0^\tau p\,dt \quad (2)$$

When the base of the test tube 14 and the metal rod 46 collide, a pressure impulse gradient ∂P/∂z occurs in the liquid surface LS1 from the basal face of the test tube 14. The pressure impulse gradient ∂P/∂z is constant irrespective of distance z in the tube axial direction. The liquid surface LS1 that has achieved the initial velocity $U_0$ is discharged as a jet of focused shape due to focusing of the flow. The jet velocity $V_{jet}$ in this case is proportional to the initial velocity $U_0$ of the test tube 14 and is expressed as:

$$V_{jet} = \beta_0 U_0 \quad (3)$$

$β_0$ herein is the velocity increase ratio of the jet velocity $V_{jet}$ with respect to the initial velocity $U_0$ (of the test tube 14)

imparted to the liquid 36 inside the test tube 14 for cases in which there is no narrow tube inserted into the test tube 14.

Figure 4B:
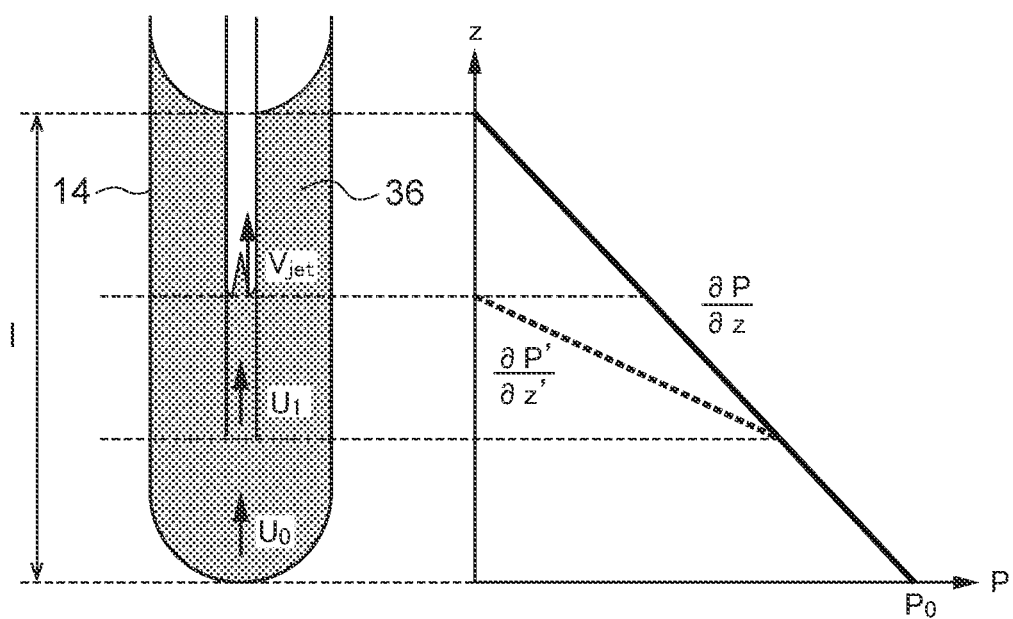
FIG. 4B is a schematic diagram of discharge of the liquid jet in a device according to the first exemplary embodiment, and a pressure impulse gradient thereof.

Next, consider a relationship between the initial velocity and the jet velocity in cases in which the narrow tube 16 has been inserted into the test tube 14 (see FIG. 4B).

The pressure impulse gradient ∂P/∂z at the basal face of the test tube 14 changes to a pressure impulse gradient ∂P'/∂z' inside the narrow tube with the bottom end face of the narrow tube 16 as a boundary. The pressure impulse gradient ∂P'/∂z' inside the narrow tube 16 is given by the following equation using the pressure impulse gradient ∂P/∂z at the basal face of the test tube 14, the first liquid level difference $l_u$, and the second liquid level difference $l_m$.

$$\frac{\partial P'}{\partial z'} = \left(\frac{l_u}{l_m} + 1\right)\frac{\partial P}{\partial z} \quad (4)$$

The initial velocity $U_1$ imparted to the liquid 36 inside the narrow tube 16 is expressed by the following equation, similarly to Equation (1).

$$U_1 = -\frac{1}{\rho}\frac{\partial P'}{\partial z'} \quad (5)$$

From Equation (1), Equation (4), and Equation (5), the initial velocity $U_1$ inside the narrow tube 16 is expressed by the following equation.

$$U_1 = -\frac{1}{\rho}\left(\frac{l_u}{l_m} + 1\right)\frac{\partial P}{\partial z} = \left(\frac{l_u}{l_m} + 1\right)U_0 \quad (6)$$

From Equation (6), the initial velocity $U_1$ imparted to the liquid 36 inside the narrow tube 16 is increased in velocity by $((l_u/l_m)+1)$ times the initial velocity $U_0$ imparted to the liquid 36 outside the narrow tube 16. The jet velocity $V_{jet}$ generated by the narrow tube 16 is, similarly to Equation (3), proportional to the initial velocity $U_1$ of the liquid 36 inside the narrow tube 16 and is expressed by the following equation.

$$V_{jet} = \beta_v U_1 = \beta_v\left(\frac{l_u}{l_m} + 1\right)U_0 = \beta U_0 \quad (7)$$

Herein, $\beta_v$ is the velocity increase ratio of the jet velocity $V_{jet}$ with respect to an initial velocity $U_1$ imparted to the liquid 36 in a narrow tube 16 for cases in which the narrow tube 16 has been inserted into the test tube 14. Moreover, $\beta$ is the velocity increase ratio of the jet velocity $V_{jet}$ with respect to an initial velocity $U_0$ (of the test tube 14) imparted to the liquid 36 in the test tube 14 for cases in which the narrow tube 16 has been inserted into the test tube 14.

From Equation (3) and Equation (7), for the same velocity increase ratios $\beta_0$, $\beta_v$, the jet velocity $V_{jet}$ of the narrow tube 16 is increased in velocity to $((l_u/l_m)+1)$ times cases in which there is no narrow tube 16 inserted into the test tube 14. Note that the velocity increase ratios $\beta_0$, $\beta_v$, are normally the same in cases in which the viscosity of the liquid 36 is the same in FIG. 4A and FIG. 4B.

In this manner, by inserting the narrow tube 16 into the test tube 14 and inducing a liquid level difference between the liquid surface LS1 outside the narrow tube 16 and the liquid surface LS2 inside the narrow tube 16, in this case by making the liquid surface LS2 higher than the liquid surface LS1, the initial velocity $U_1$ imparted to the liquid 36 inside the narrow tube 16 may be increased in velocity compared to the initial velocity $U_0$ with the test tube 14 alone. This enables the jet velocity $V_{jet}$ generated in the narrow tube 16 to also be increased in velocity compared to the Comparative Example (the test tube 14 alone).

Namely, the velocity increase ratio $\beta$ of the jet velocity $V_{jet}$ may be raised by increasing the first liquid level difference $l_u$, or by reducing the second liquid level difference $l_m$.

Note that the viscosity v of the liquid 36 only has an effect on the velocity increase ratio $\beta_v$.

Tests

The following tests were performed to confirm the operation described above and considerations based on the analysis model.

The liquid jet discharge device 10 according to the Example employed the same configuration to that illustrated in FIG. 1.

The test tube 14 was made from borosilicate glass (hard glass A-16-5 manufactured by Maruemu Corporation) with a semi-spherical shaped basal face. The liquid 36 employed was silicone oil (manufactured by Sigma Ardlich Co.).

In the tests, a high speed camera (FASTCAM SA-X, manufactured by Photron Co.) and a light source (LLUB White Led BACKLIGHT, manufactured by Phlox Co.) was employed. The imaging speed was 25,000 fps.

Note that in the tests, the time when the liquid jet MJ was confirmed with the high speed camera to have started to project from the horizontal liquid surface LS2 was taken as t=0 ms. The change in time of displacement of the jet leading end confirmed by the high speed camera confirmed from t=0 ms to t=0.32 ms was approximated into straight line, and the slope of the straight line was taken as jet velocity $V_{jet}$.

Similarly, the change in time of the displacement of the test tube 14 confirmed by the high speed camera from t=0 ms to t=0.32 ms was approximated into straight line, and the slope of the straight line was taken as initial velocity $U_0$ imparted to the liquid 36.

In the tests, liquids 36 with viscosities within the respective ranges listed in Table 1 were placed in the test tube 14, and the jet velocity $V_{jet}$ of the liquid jet MJ discharged from the narrow tube 16 was measured. In the top row, only the viscosity of the liquid 36 was changed, and in the three rows below the top row, the viscosity of the liquid 36 and one of the first to the third liquid level differences $l_u$, $l_m$, or $l_b$ were changed.

TABLE 1

| $U_0$ (m/s) | D (mm) | d (mm) | v (mm²/s) | lb (mm) | lm (mm) | lu (mm) |
|---|---|---|---|---|---|---|
| 0.2-1.9 | 8 | 2 | 1-1000 | 7 | 3 | 10 |
| | | | 1-100 | 7 | 3 | 4-19 |
| | | | | 7 | 1-15 | 10 |
| | | | | 4-19 | 3 | 10 |
| | | 0.5 | 10-500 | 7 | 3 | 4-19 |

1. Relationship of Jet Velocity $V_{jet}$ to the First Liquid Level Difference $l_u$.

Figure 5:
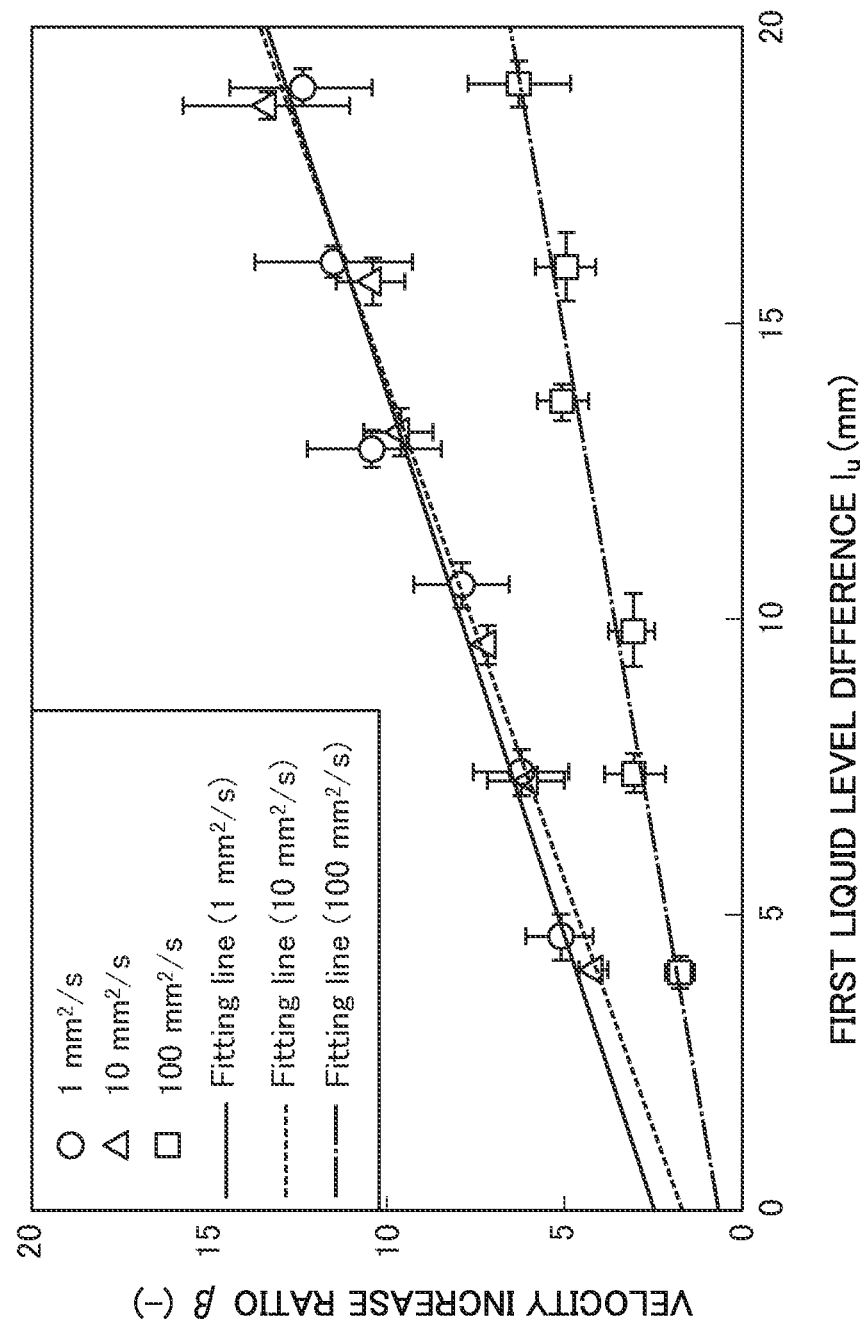
FIG. 5 is a graph illustrating relationships in the liquid jet discharge device according to the first exemplary embodiment between a velocity increase ratio and a first liquid level difference between a liquid surface outside a narrow tube in a test tube and a liquid surface inside the narrow tube.

FIG. 5 illustrates the relationships between the velocity increase ratio $\beta$ (=$V_{jet}/U_0$) and the first liquid level difference $l_u$. The respective viscosities are indicated with white circles for 1 mm²/s, with white triangles for 10 mm²/s, and with white squares for 100 mm²/s. Testing was performed five times under the same conditions, their average values were then plotted with their standard deviations employed for the error bars. The same applies to FIG. 6 to FIG. 12 below.

At each of the viscosities v, the velocity increase ratio β increased as the first liquid level difference $l_u$ increased. Moreover, from Equation (7), the velocity increase ratio β and the first liquid level difference $l_u$ may be expected to be linear functions. The results of linear fitting are thus indicated here by straight lines. Confirmation could be made that the test results were well represented by a straight line at each of the viscosities v.

Figure 6:
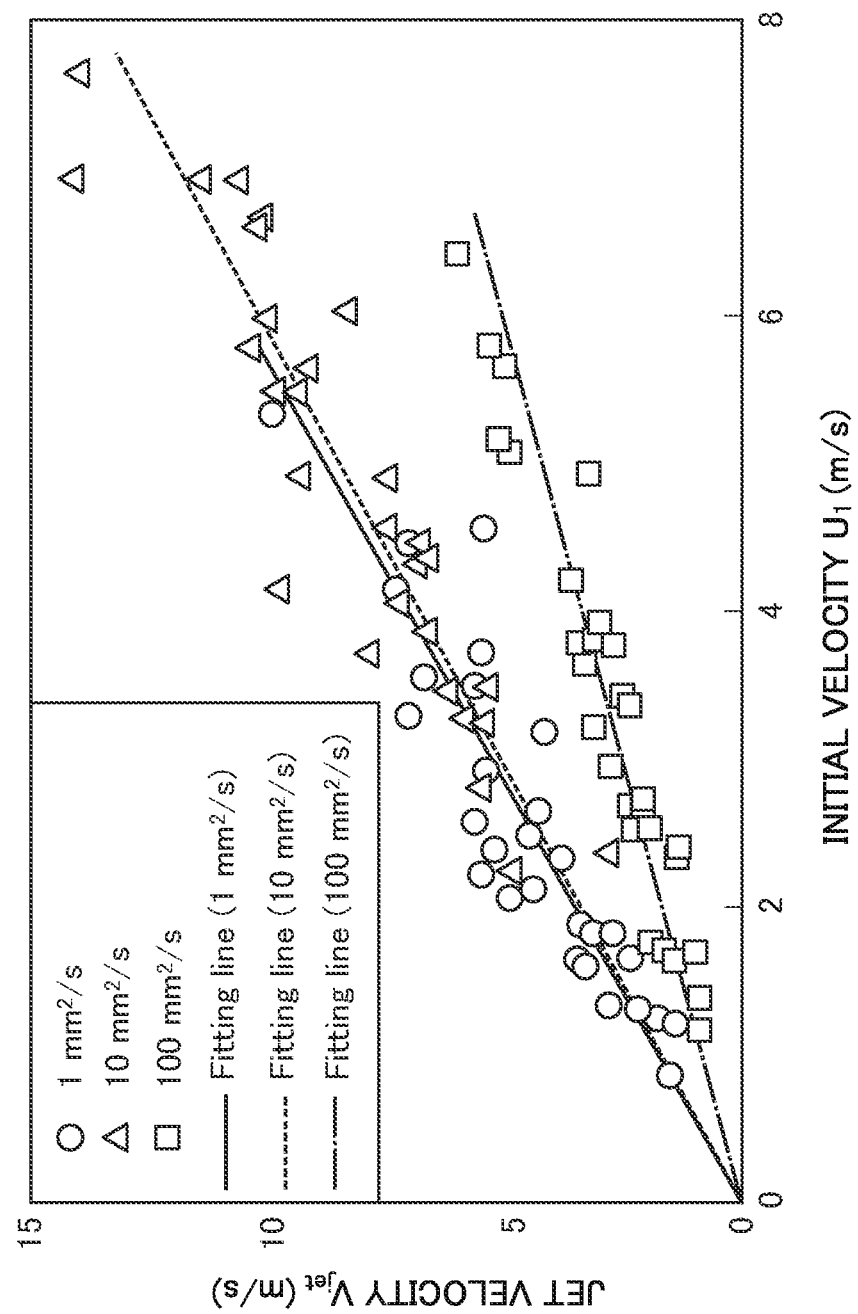
FIG. 6 is a graph illustrating relationships in the liquid jet discharge device according to the first exemplary embodiment between initial velocity of the narrow tube and jet velocity.

These results were rearranged using Equation (7), and relationships between the jet velocity $V_{jet}$ and the initial velocity $U_1$ imparted to the liquid 36 in the narrow tube 16 are illustrated in FIG. 6. Note that the initial velocity $U_1$ imparted to the liquid 36 in the narrow tube 16 is computed by Equation (6). At each of the viscosities v, the jet velocity $V_{jet}$ increased as the initial velocity $U_1$ imparted to the liquid 36 in the narrow tube 16 increased. The results of linear fitting using Equation (7) are indicated by the straight lines in FIG. 6. Confirmation could be made that the test results were well represented by Equation (7) at each of the viscosities v. Namely, confirmation could be made that the test results satisfied Equation (7), and that the test results could be explained by the model described above.

Note that, as illustrated in FIG. 5, the jet velocity $V_{jet}$ was confirmed to be a maximum of about 12 times the initial velocity $U_0$ imparted to the test tube 14. This amounts to a large increase in velocity compared to a jet velocity of about 1.7 times the initial velocity $U_0$ in cases in which a traditional device (a device with the test tube 14 alone) was employed.

Note that for cases in which the inner diameter d of the narrow tube 16 in Table 1 was 0.5 mm, and the viscosity v of the liquid 36 was 10 mm$^2$/s, 100 mm$^2$/s, or 500 mm$^2$/s, relationships between "$(l_u/l_m)+1$" and velocity increase ratio β were found by changing the first liquid level difference $l_u$ under similar test conditions. These results are illustrated in FIG. 18.

Figure 18:
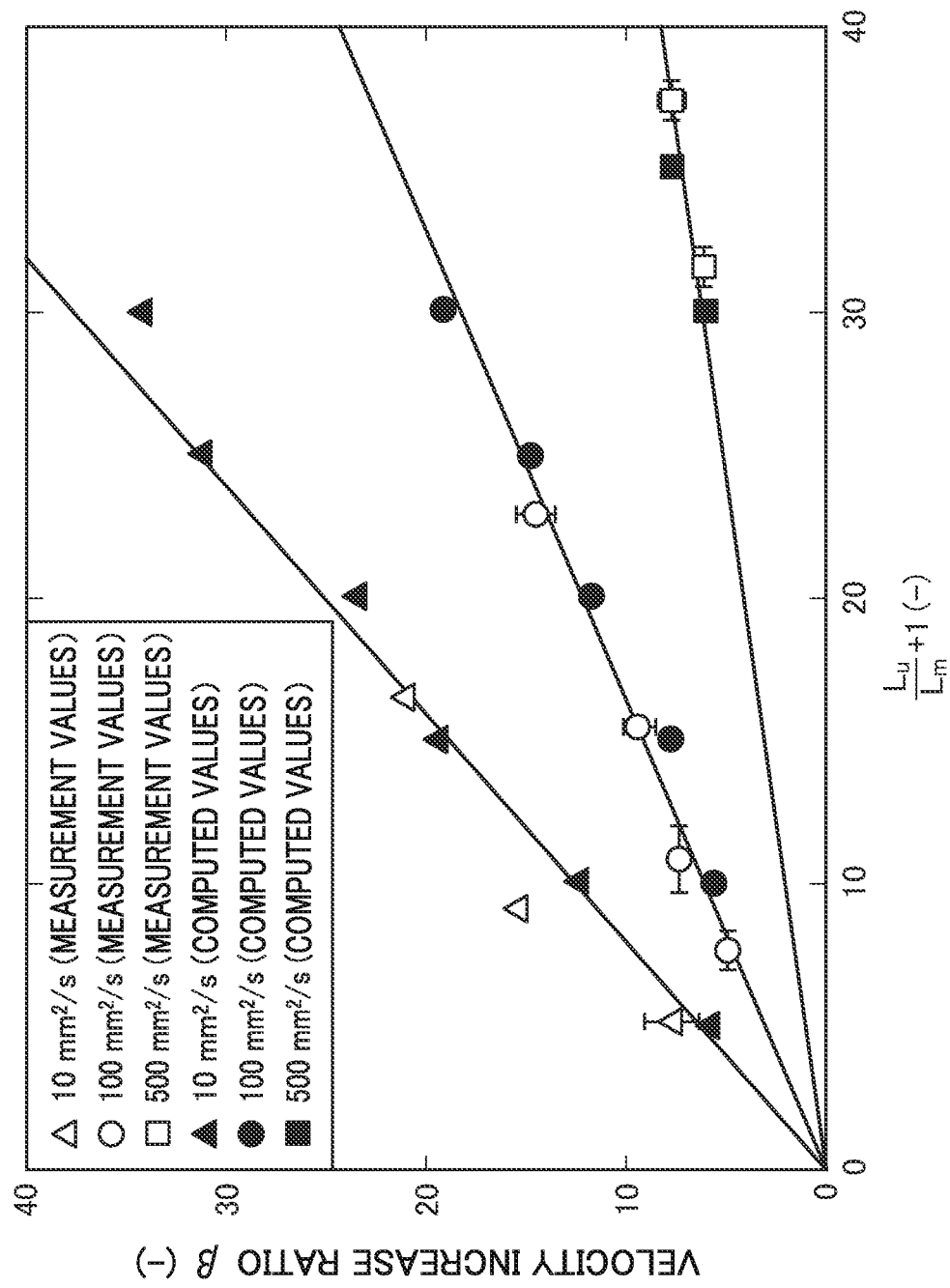
FIG. 18 is a graph illustrating relationships in the liquid jet discharge device according to the first exemplary embodiment between a velocity increase ratio and first liquid level differences and second liquid level differences for different inner diameters of narrow tube.

Note that in FIG. 18, the respective viscosities are indicated by white circles for 10 mm$^2$/s, with white triangles for 100 mm$^2$/s, and with white squares for 500 mm$^2$/s. Testing was performed five times under the same conditions, their average values were then plotted with their standard deviations employed for the error bars. Calculated values for each of the viscosities are indicated by black triangles for 10 mm$^2$/s, black circles for 100 mm$^2$/s, and black squares for 500 mm$^2$/s.

The results of linear fitting are indicated by straight lines. Confirmation was made that the test results and the calculation results for each viscosity v could be well represented by straight lines.

Figure 7:
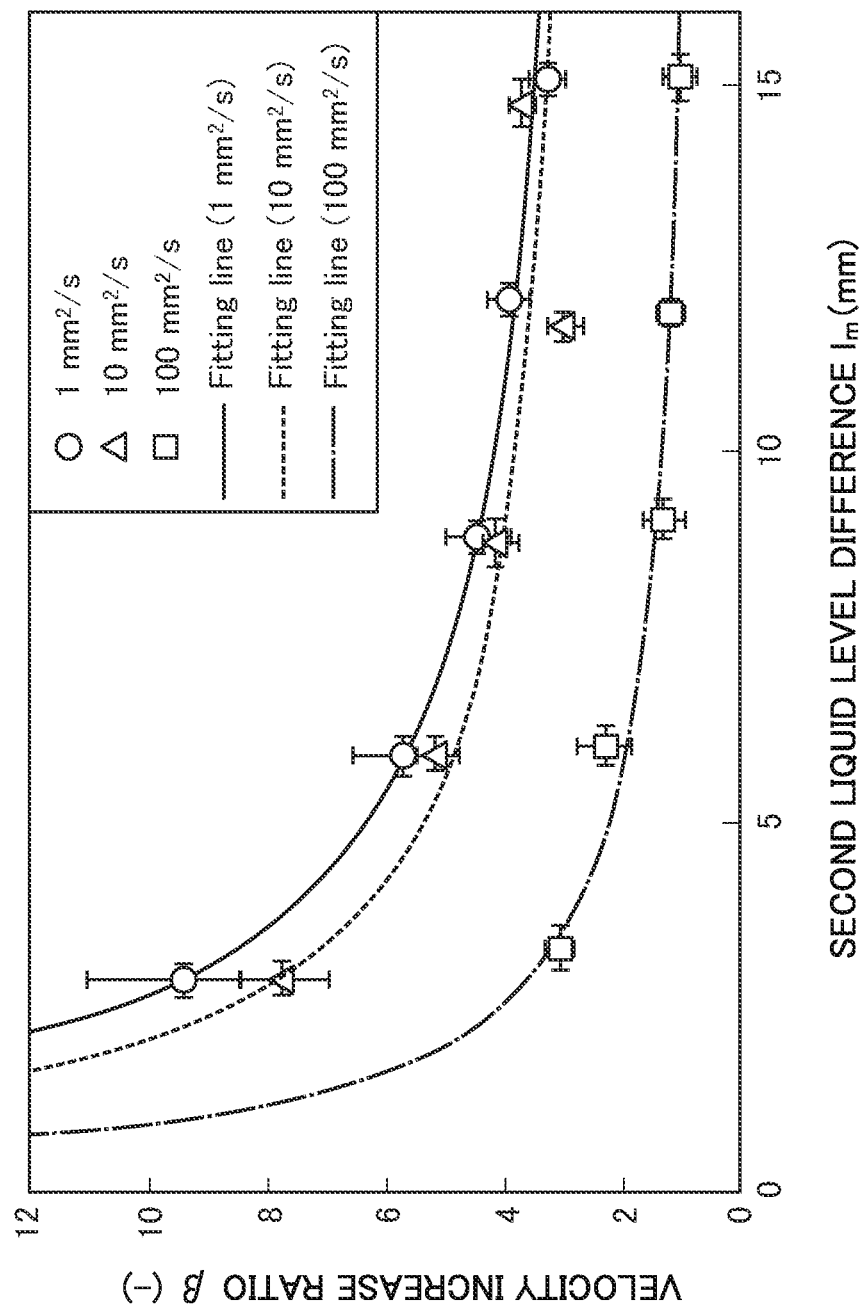
FIG. 7 is a graph illustrating relationships in the liquid jet discharge device according to the first exemplary embodiment between a velocity increase ratio and a second liquid level difference between a liquid surface inside the narrow tube and a bottom end face of the narrow tube.

2. Relationship Between Jet Velocity $V_{jet}$ and Second Liquid Level Difference $l_m$ FIG. 7 illustrates relationships between the velocity increase ratio β and the second liquid level difference $l_m$. However, in test conditions in which $l_m$=1 mm, the pressure impulse gradient $\partial P'/\partial z'$ inside the narrow tube 16 falls within a transition region, and since the analysis model is no longer applicable, these test conditions are omitted.

At each of the viscosities v, the velocity increase ratio β decreased as the second liquid level difference $l_m$ increased. From Equation (7), it may be expected that the velocity increase ratio β and the second liquid level difference $l_m$ would have an inverse proportional relationship to each other. The velocity increase ratio β is thus expressed by Equation (8) using fitting parameters A, B.

$$\frac{V_{jet}}{U_0} = \frac{A}{l_m} + B \tag{8}$$

Fitting of Equation (8) to the test results is illustrated in FIG. 7. At each of the viscosities v, the trend in the test results were well represented by Equation (8). Thus, the velocity increase ratio β and the second liquid level difference $l_m$ have an inverse proportional relationship to each other.

Figure 8:
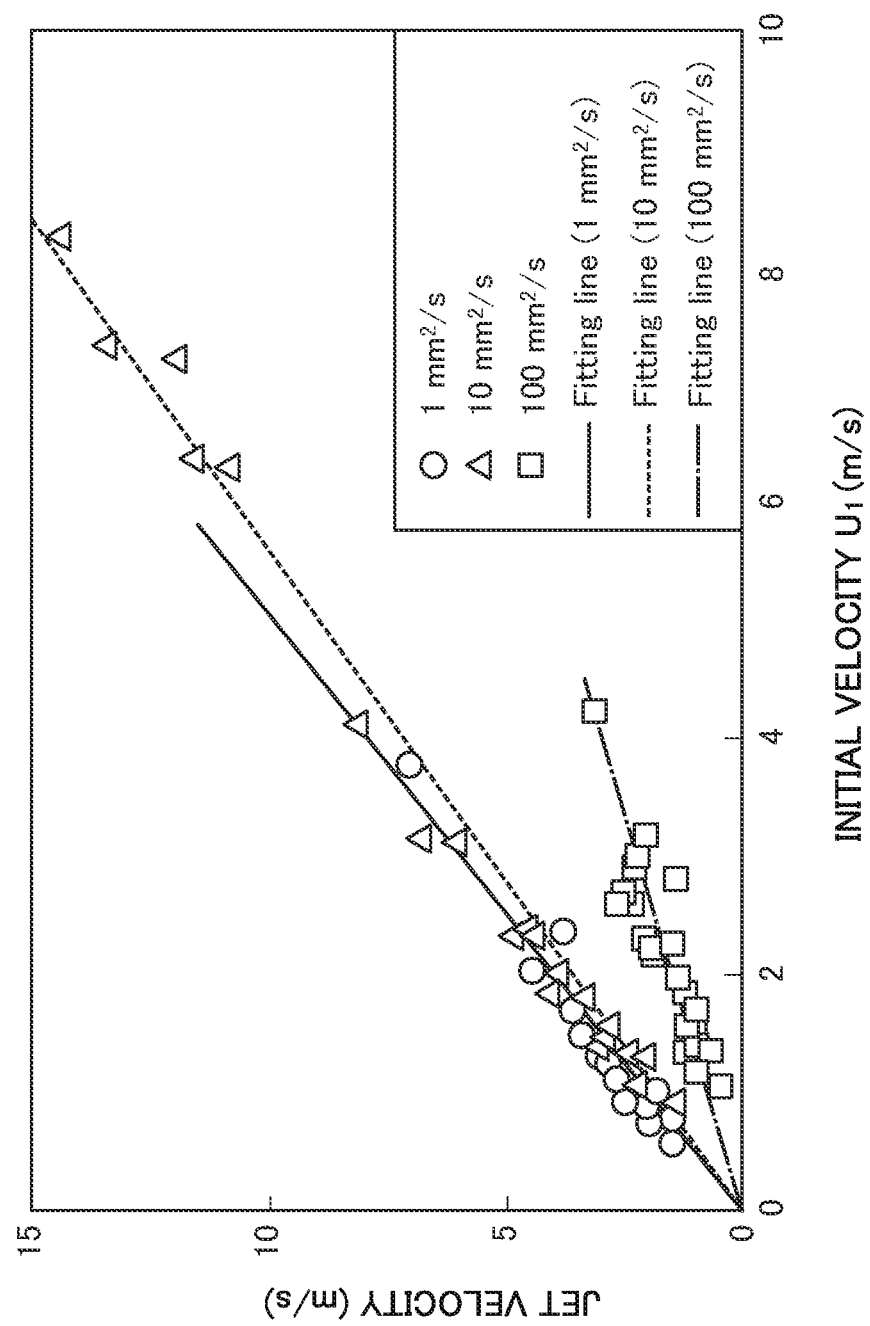
FIG. 8 is a graph illustrating relationships in the liquid jet discharge device according to the first exemplary embodiment between narrow tube initial velocity and jet velocity.

Rearranging this result using Equation (7) gives the relationship between jet velocity $V_{jet}$ and the initial velocity $U_1$ imparted to the liquid 36 in the narrow tube 16 as illustrated in FIG. 8. At each of the viscosities v, the jet velocity $V_{jet}$ increased with an increase in the initial velocity $U_1$ imparted to the liquid 36 in the narrow tube 16. The results of fitting with Equation (7) are indicated by straight lines in FIG. 8. Confirmation was made that the test results could be well represented by Equation (7) at each of the viscosities v. Namely, confirmation was made that the test results satisfied Equation (7), and that the test results could be explained by the model described above.

Note that the maximum velocity in the tests was measured as a jet velocity $V_{jet}$=14.3 m/s at a viscosity v=10 mm$^2$/s, and an initial velocity $U_1$=8.25 m/s, where $U_1$ is the initial velocity imparted to the liquid 36 in the narrow tube 16.

Figure 9:
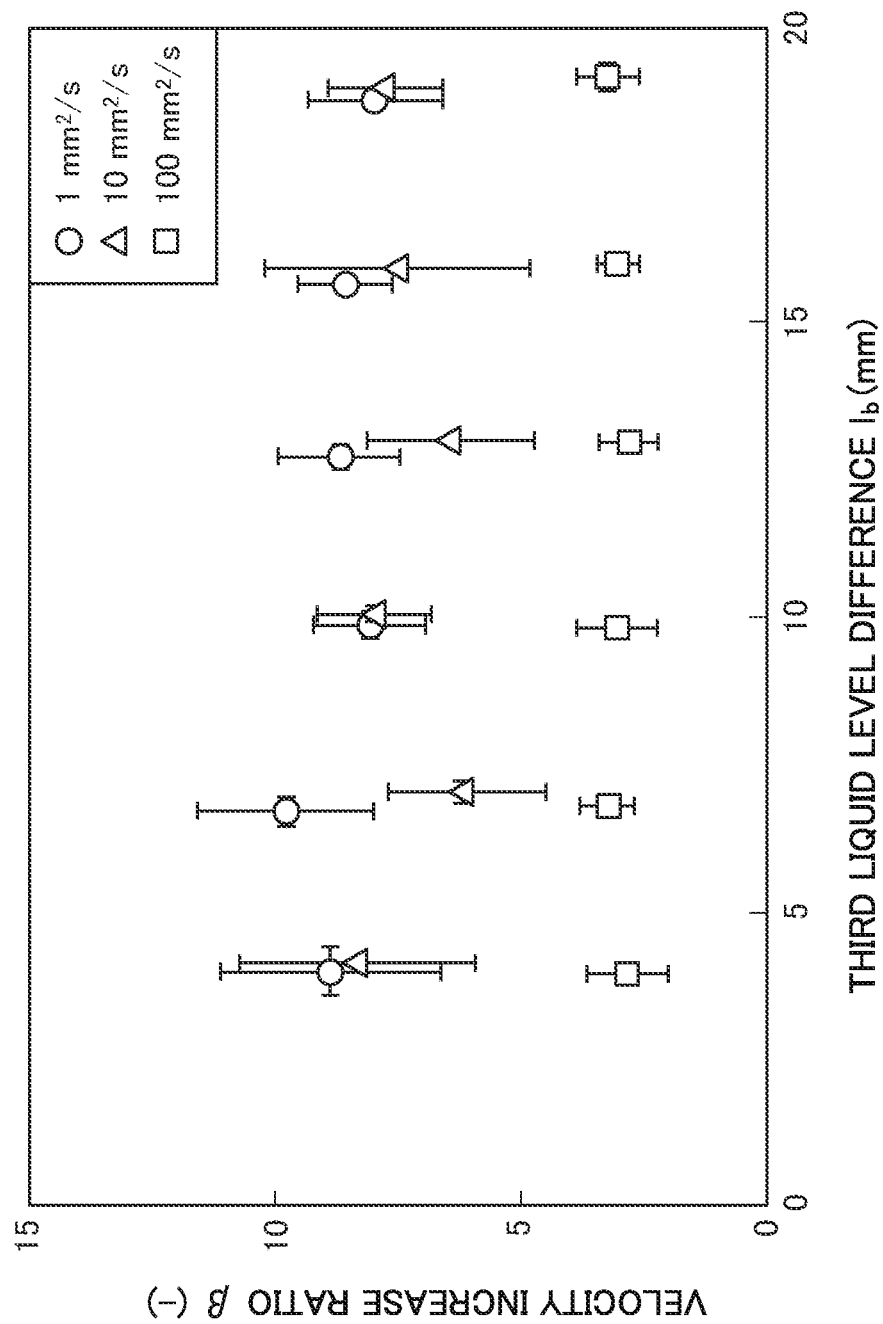
FIG. 9 is a graph illustrating relationships in the liquid jet discharge device according to the first exemplary embodiment between a velocity increase ratio and a third liquid level difference between the bottom end face of the narrow tube and a basal face of the test tube.

3. Relationship Between Jet Velocity $V_{jet}$ and Third Liquid Level Difference $l_b$ The relationship between the velocity increase ratio β and the third liquid level difference $l_b$ are illustrated in FIG. 9. At each of the viscosities v, the velocity increase ratio β was substantially constant even when the third liquid level difference $l_b$ changed. This matches the model.

Figure 10:
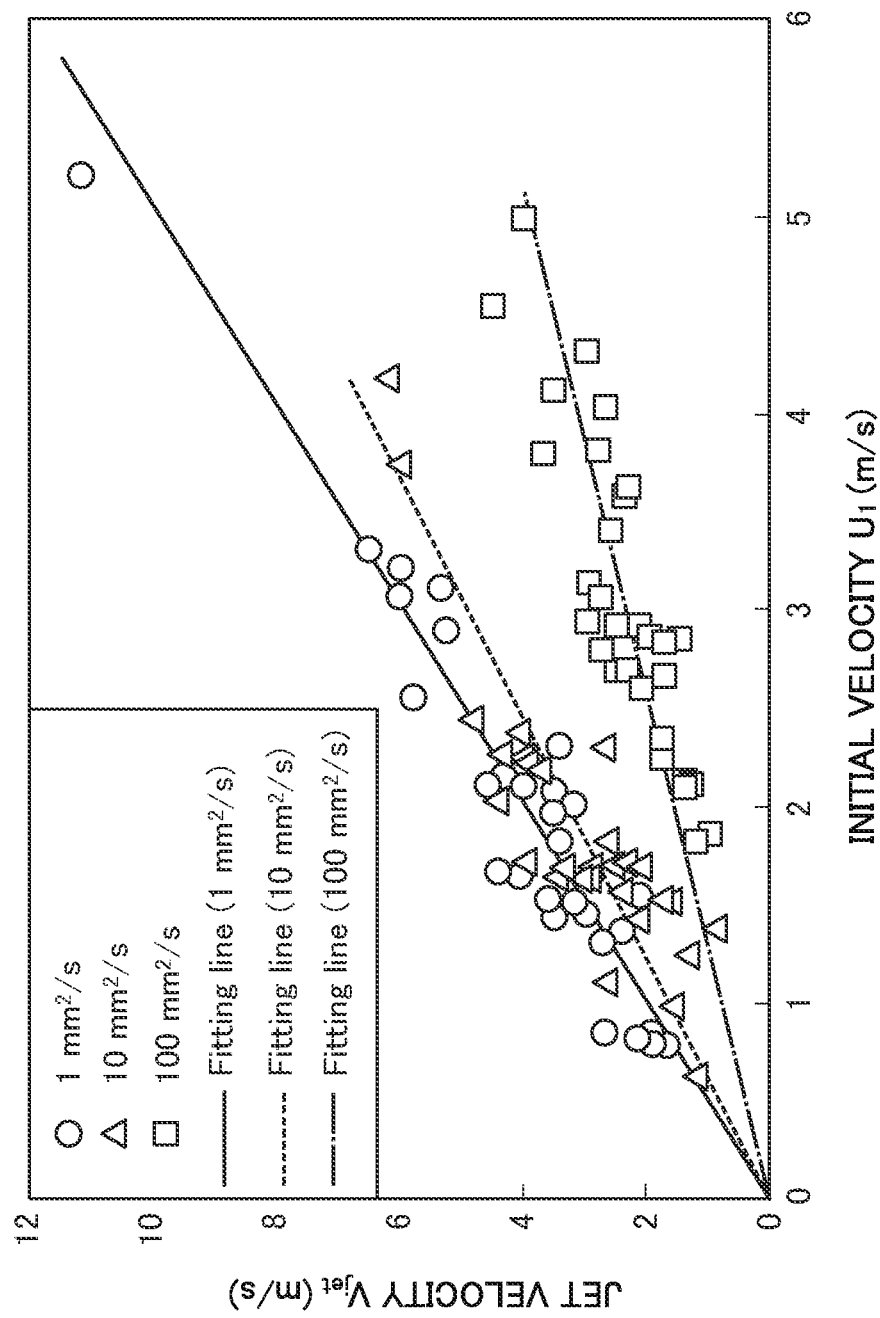
FIG. 10 is a graph illustrating relationships in the liquid jet discharge device according to the first exemplary embodiment between initial velocity of the narrow tube and jet velocity.
Figure 11:
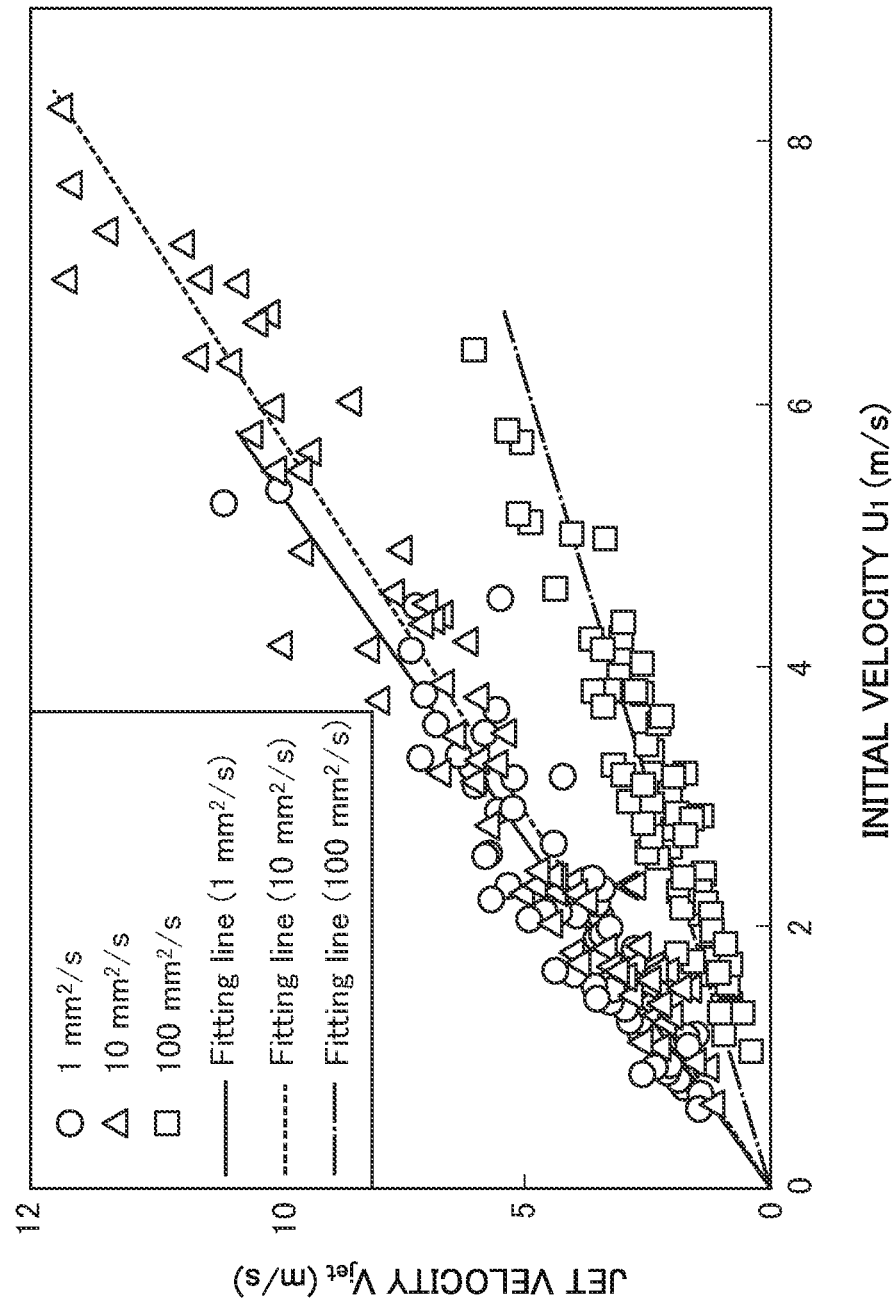
FIG. 11 is a graph combining FIG. 6, FIG. 8, and FIG. 10.

Rearranging the results using Equation (7) gives the relationship between jet velocity Vjet and the initial velocity $U_1$ imparted to the liquid 36 in the narrow tube 16 as illustrated in FIG. 10. At each of the viscosities v, the jet velocity $V_{jet}$ increased as the initial velocity $U_1$ imparted to the liquid 36 in the narrow tube 16 increased. The results of fitting with Equation (7) are indicated by straight lines in FIG. 10. Confirmation was made that the test results could be well represented by equation (7) at each of the viscosities v. Namely, confirmation was made that the test results satisfied Equation (7), and that the test results could be explained by the model.

4. Relationships Between Jet Velocity $V_{jet}$ and First Liquid Level Difference $l_u$, Second Liquid Level Difference $l_m$, and Third Liquid Level Difference $l_b$ All of the results of FIG. 6, FIG. 8, and FIG. 10 are combined in FIG. 11. The results of fitting the test results with Equation (7) are indicated by straight lines in FIG. 11. At each of the viscosities v, the trend in the test results could be well represented by Equation (7). Thus, all of the test results may be explained by the model even in cases in which the first liquid level difference $l_u$, the second liquid level difference $l_m$, or the third liquid level difference $l_b$ are respectively changed.

5. Relationship Between Jet Velocity $V_{jet}$ and Viscosity v.

Figure 12:
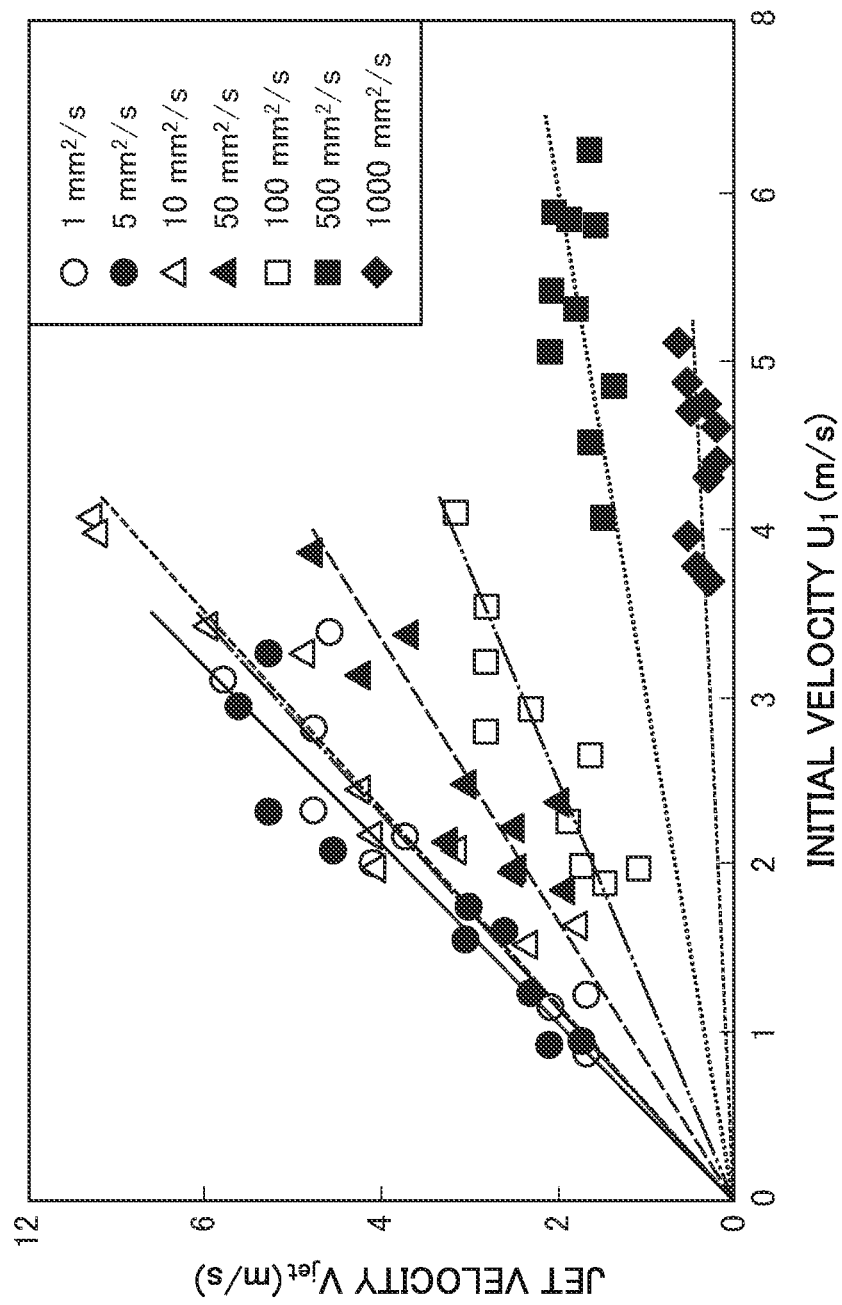
FIG. 12. is a graph illustrating relationships in the liquid jet discharge device according to the first exemplary embodiment between jet velocity of a liquid having a viscosity in the range of from 1 mm²/s to 100 mm²/s and initial velocity of the narrow tube.

FIG. 12 illustrates relationships between the jet velocity $V_{jet}$ of liquids 36 having a range of viscosities of from 1 mm$^2$/s to 1000 mm$^2$/s and the initial velocity $U_1$ imparted to the liquid 36 in the narrow tube 16. In FIG. 12, viscosities of 5 mm$^2$/s, 50 mm$^2$/s, 500 mm$^2$/s, and 1000 mm$^2$/s are indicated by black circles, black triangles, black squares, and black diamonds, respectively. The white circles, white triangles, and white squares indicate the same as those in FIG. 5. Note that the initial velocity $U_1$ imparted to the liquid 36 in the narrow tube 16 was computed by Equation (6). The results of fitting with Equation (7) are indicated by each of the lines. At each of the viscosities v, the trend in the test results could be well represented by Equation (7). The jet velocity $V_{jet}$ and the initial velocity $U_1$ imparted to the liquid 36 in the narrow tube 16 hold a proportional relationship to each other. Thus the test results satisfy Equation (7).

Note that in the present tests, as illustrated in FIG. 12, confirmation was made that a jet of tapered shape could be generated from liquids 36 of high viscosity (1000 mm$^2$/s).

However, for viscosities v exceeding 10 mm$^2$/s, the velocity increase ratio $\beta_v$ (the angle of slope of the line in FIG. 12) is reduced. Consider the following regarding the relationship between the viscosity v and the velocity increase ratio $\beta_v$.

Figure 13:
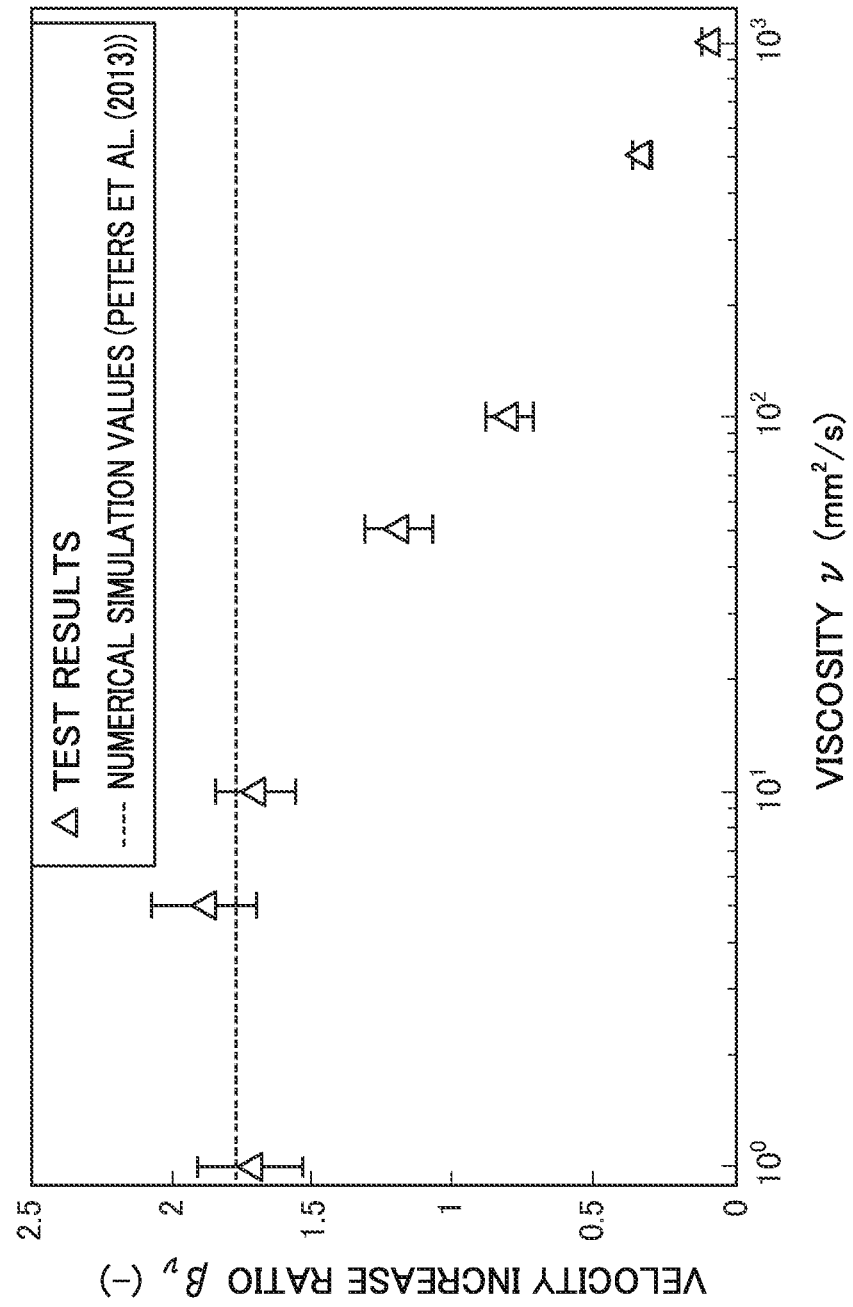
FIG. 13 is a graph illustrating relationships in the liquid jet discharge device according to the first exemplary embodiment between viscosity and velocity increase ratio.

FIG. 13 illustrates the relationship between viscosity v and velocity increase ratio $\beta_v$. The velocity increase ratio obtained by numerical simulation ignoring viscosity v (as described in the paper titled: Highly focused supersonic microjets: numerical simulations, by I. R Peters, Y. Tagawa, N. Oudalov, D. van der Meer, C. Sun, A. Prosperetti, and D. Lohsein the Journal of Fluid Mechanics, No. 719, pp. 587 to 605, January 2013) is indicated by the broken line in FIG. 13. The velocity increase ratio $\beta_v$ obtained by the test results in the range of viscosities from 1 mm$^2$/s to 10 mm$^2$/s have good match with the velocity increase ratio obtained by numerical simulation. This leads to the thought that the influence of viscosities v on velocity increase ratio $\beta_v$ is small in the range of viscosities from 1 mm$^2$/s to 10 mm$^2$/s, and may thus be ignored.

However, in the range of viscosities from 50 mm$^2$/s to 1000 mm$^2$/s, the velocity increase ratio $\beta_v$ falls as the viscosity v increases. This leads to the thought that the viscosity v contributes to a fall in the velocity increase ratio $\beta_v$ in the range of viscosities from 50 mm$^2$/s to 1000 mm$^2$/s.

Cavitation Effect

Non-Patent Document 4 describes that a jet velocity $V_{jet}$, when the liquid surface of a fluid blob (diameter d, height l) has formed a concave surface shape, depends only on the initial velocity $U_0$ imparted to the fluid blob, and does not depend on the diameter d and the height l of the fluid blob, if the contact angle $\theta$ is fixed, as expressed by Equation (9).

$$V_{jet} = \beta U_0$$

$$\beta = 1 + \alpha \cos \theta \quad (9)$$

Figure 14:
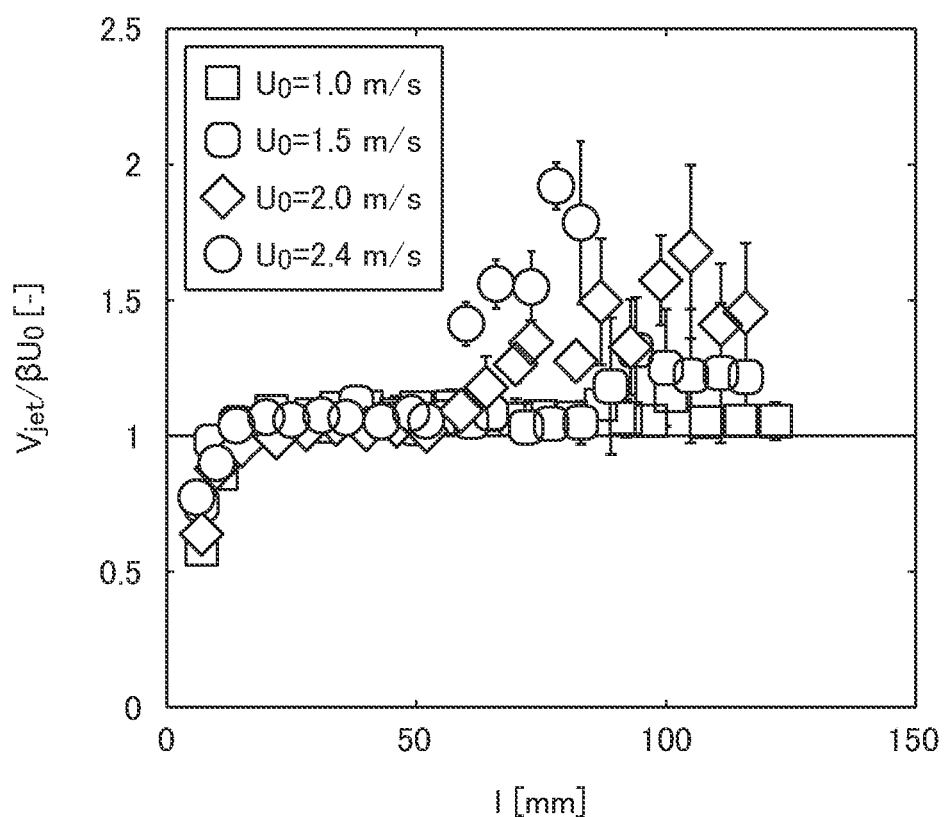
FIG. 14 is a graph illustrating relationships between height of liquid surface (liquid surface) and velocity increase ratio.

Moreover, as illustrated in FIG. 14, there is a large increase in velocity of a jet when l≥50.0 mm and $U_0$=1.5 m/s, 2.0 m/s, and 2.4 m/s, and this is thought to occur due to a phenomenon related to cavitation.

Cavitation as described here is thought to be generated in cases in which a large acceleration is imparted to a liquid, and localized pressure within the liquid becomes the vapor pressure of the liquid 36 or lower. Assuming an incompressible liquid 36, the momentum of the liquid 36 changes over the time scale $\Delta t_i$. The position where the pressure falls the most due to this change in momentum is the basal face of a test tube. Considering the pressure at the basal face of the test tube, Non-Patent Document 4 describes that cavitation bubbles may be generated immediately after the momentum change when the following equation is satisfied:

$$Pv \geq (P_{atm} + \rho lg) - \frac{\rho l U_0}{\Delta t_i} = P_{atm} + \rho l(g-a) \quad (10)$$

where $P_{atm}$ is atmospheric pressure, Pv is vapor pressure of the liquid 36, and $\rho$ is density of the liquid 36.

It is thought that the present invention may be applied to increase the velocity of the liquid jet by intentionally generating cavitation by using the relationship between initial velocity $U_0$ and the liquid surface heights l ($l_u+l_m+l_b$) such that these conditions (Equation (10)) are satisfied.

Summary

As described above, in the liquid jet discharge device 10 according to the present exemplary embodiment, the narrow tube 16 is inserted into the test tube 14, and the liquid surface LS2 formed inside the narrow tube 16 is caused to adopt a concave shape due to the liquid 36 contacting the narrow tube 16 at a contact angle $\theta$ of less than 90 degrees, such that when impulse force from the metal rod 46 acts on the test tube 14, flow is focused at the liquid surface LS2. As a result, an accelerated long, thin liquid jet MJ having a tapered shape is discharged from the vicinity of the central axis of the liquid surface LS2.

In particular, the velocity increase ratio $\beta$ may be increased by inducing the first liquid level difference $l_u$ between the liquid surface LS2 inside the narrow tube 16 and the liquid surface LS1 outside the narrow tube 16, in this case by setting the liquid surface LS2 lower than the liquid surface LS1. As a result, a high speed liquid jet may be discharged by a fixed impulse force.

Moreover, the jet velocity $V_{jet}$ may be changed by changing the velocity increase ratio $\beta$ by changing the first liquid level difference $l_u$ between the liquid surface LS2 inside the narrow tube 16 and the liquid surface LS1 outside the narrow tube 16. Namely, the jet velocity $V_{jet}$ of the liquid jet discharge device 10 may be controlled.

For example, it is thought that the jet velocity $V_{jet}$ may be reduced in speed relative to the initial velocity $U_0$ by making the liquid surface LS2 inside the narrow tube 16 higher than the liquid surface LS1 outside the narrow tube 16.

Furthermore, there are few components in the liquid jet discharge device 10, i.e., the coilgun 18 to impart the impulse force to the liquid 36, the syringe pump 20 to induce the first liquid level difference $l_u$ between the liquid surface LS1 and the liquid surface LS2, etc. The device configuration is accordingly simplified. Thus, the ease of operation is better than that of devices employing lasers or the like.

In this manner, a high proportion of energy from a fixed amount of energy imparted to the liquid 36 may be intensified in the liquid jet MJ by discharging the high speed liquid jet MJ with a high velocity increase ratio $\beta$. Namely, due to being able to discharge the fast liquid jet MJ, the energy loss in high viscosity liquids (for example, 1000 mm$^2$/s) due to viscous forces may be overcome, enabling high viscosity liquids to be discharged.

Note that such a liquid jet discharge device 10 is thought to have uses in ink jetting and in needleless injectors.

For example, in cases in which application is made to ink jetting, ink clogging and the like may be suppressed due to the long, thin liquid jet MJ being discharged from a central portion of the liquid surface LS2. This enables high viscosity pigment based inks to be ejected that have not been possible to eject in traditional ink jet printers. Moreover, high precision printing and the like is enabled due to the long, thin liquid jet MJ being ejected from the narrow tube 16.

Meanwhile, the liquid jet discharge device 10 is thought to be applicable to a needleless injector since the delivery position of a medicine, such as a subcutaneous or intramuscular position, may be controlled due to both being able to eject the high speed liquid jet MJ and being able to control the jet velocity $V_{jet}$.

Note that in the liquid jet discharge device 10, due to the connection tube 40 being connected to the top end of the narrow tube 16, in a case of placing a discharge target for the liquid jet MJ, for example, a pressure regulated chamber including may be provided, with a space so as to enable placement of the discharge target in place of the connection tube 40.

Second Exemplary Embodiment

A liquid jet discharge device according to a second exemplary embodiment of the present invention will now be described, with reference to FIG. 2. The same reference numerals are appended to similar components to those of the first exemplary embodiment, and description thereof will be omitted. Only points differing from the first exemplary embodiment will be described.

Figure 2:
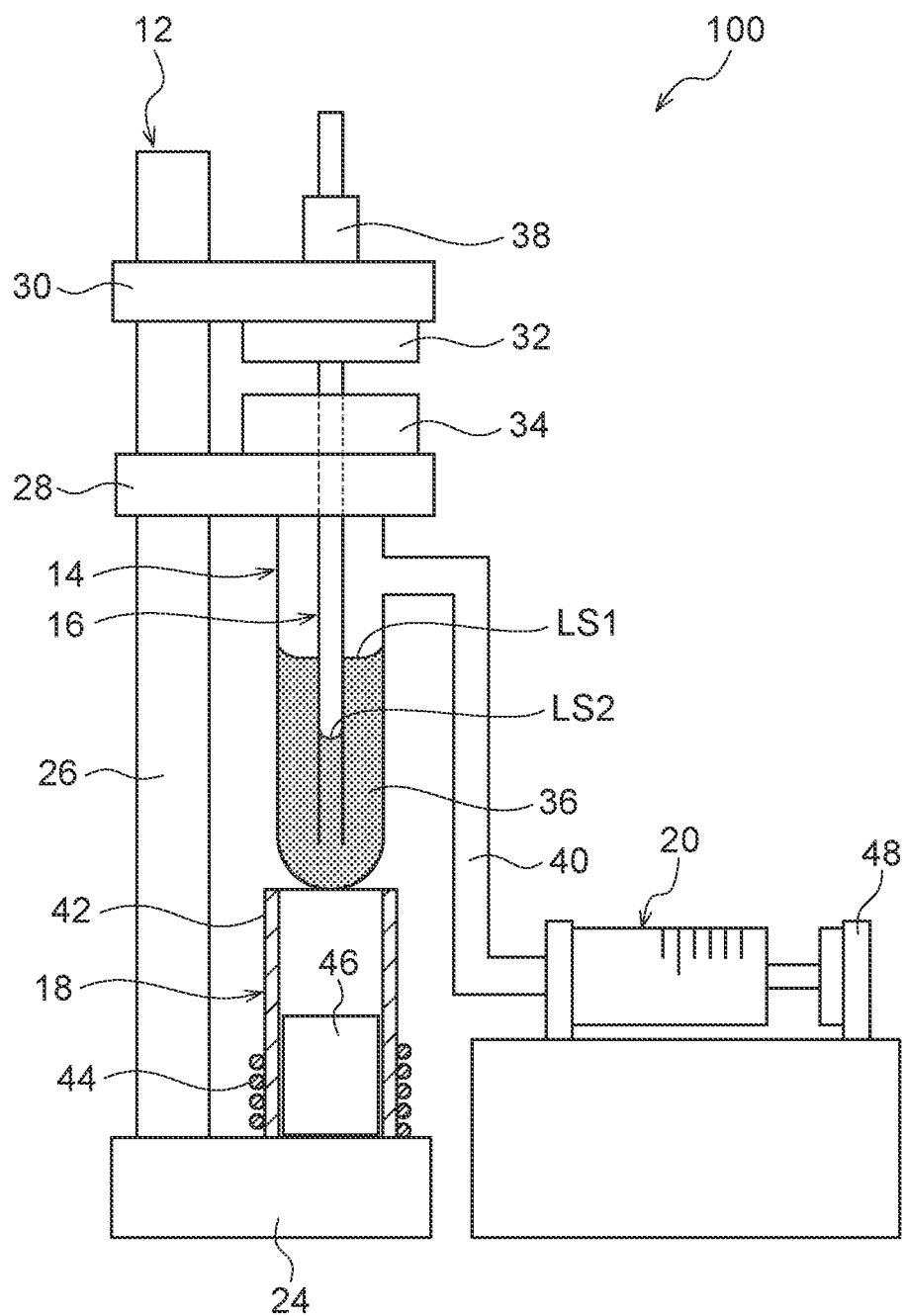
FIG. 2 is a schematic configuration diagram of a liquid jet discharge device according to a second exemplary embodiment.

As illustrated in FIG. 2, an upper portion of a narrow tube 16 of a liquid jet discharge device 100 is open to the atmosphere. However, a test tube 14 is connected to a syringe pump 20 by a connection tube 40.

Thus, the liquid surface LS1 outside the narrow tube 16 may be raised by driving the syringe pump 20 and reducing the pressure of a gas portion inside the test tube 14 and outside the narrow tube 16, thereby enabling a first liquid level difference $l_u$ to be induced between the liquid surface LS1 and the liquid surface LS2.

In this manner, the liquid jet discharge device 100, similarly to the liquid jet discharge device 10 according to the first exemplary embodiment, is able to discharge a long, thin liquid jet MJ at a high velocity increase ratio β from the liquid surface LS2 inside the narrow tube 16.

Moreover, the liquid jet discharge device 100 has a particular effect of facilitating the placement of a discharge target for the liquid jet MJ at the upper portion of the narrow tube 16, due the top end of the narrow tube 16 being open to the atmosphere since the outside of the narrow tube 16 in the test tube 14 is connected to the syringe pump 20.

Figure 15:
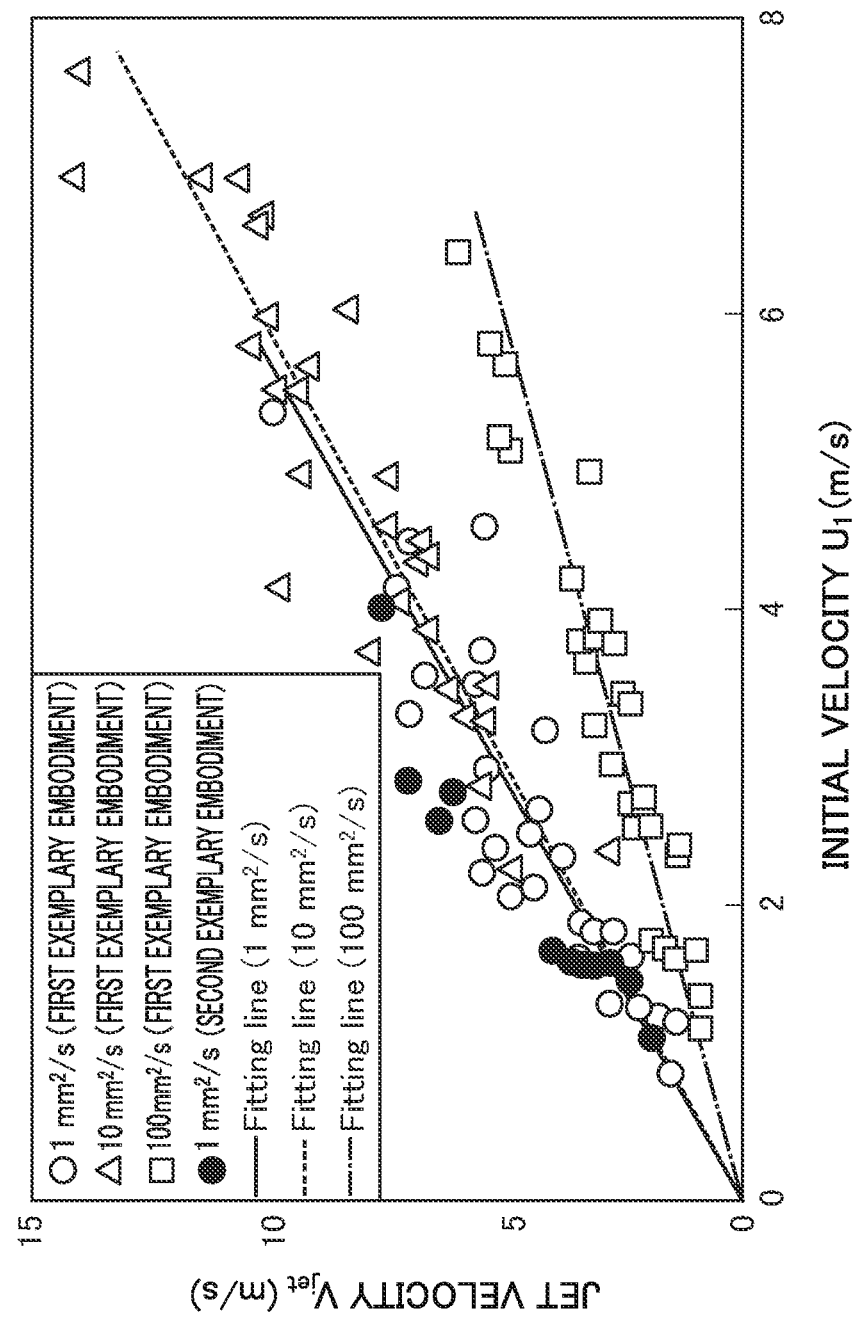
FIG. 15 is graph in which relationships in the liquid jet discharge device according to the second exemplary embodiment between initial velocity of a narrow tube and jet velocity, superimposed on FIG. 6.

Note that, similarly to in the first exemplary embodiment, the relationship between the initial velocity $U_1$ imparted to the liquid 36 inside the narrow tube 16 (viscosity: 1 mm²/s, see the black circles in FIG. 15) and the jet velocity $V_{jet}$ of the liquid jet MJ was investigated by inducing a liquid level difference between the liquid surface LS1 outside the narrow tube 16 and the liquid surface LS2 inside the narrow tube 16 and causing impulse force to act on the test tube 14 using the metal rod 46. As illustrated in FIG. 15, confirmation of a proportional relationship was also made in such cases, similarly to in the first exemplary embodiment.

Third Exemplary Embodiment

A liquid jet discharge device according to a third exemplary embodiment of the present invention will now be described, with reference to FIG. 16. The same reference numerals are appended to similar components to those of the first exemplary embodiment, and description thereof will be omitted. Only points differing from the first exemplary embodiment will be described.

Figure 16:
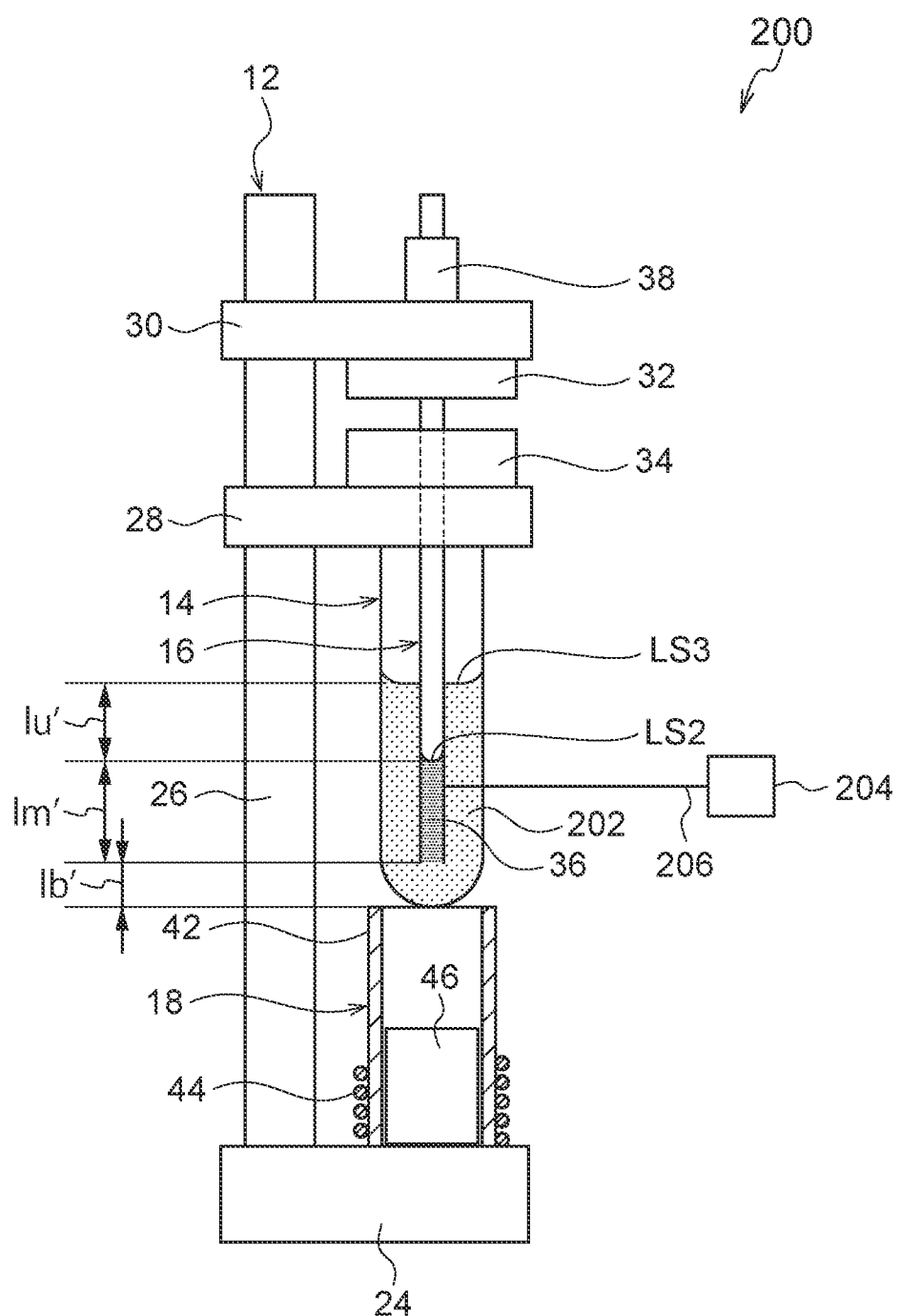
FIG. 16 is a schematic diagram of a liquid jet discharge device according to a third exemplary embodiment.

As illustrated in FIG. 16, a liquid jet discharge device 200 has a liquid 36 for discharge disposed inside a narrow tube 16, and has gelatin 202 as an example of a solid body serving as a transmission medium disposed inside the test tube 14 (at the outside of the narrow tube 16).

More specifically, the gelatin 202 is caused to flow inside the test tube 14 such that the gelatin 202 does not flow into the narrow tube 16, and after the pressure inside the test tube 14 has been raised and the gelatin 202 has been coagulated, the liquid 36 is fed inside the narrow tube 16 from a liquid feed device 204, described later. Thus, by controlling the amount of the liquid 36 fed from the liquid feed device 204 to the narrow tube 16, a first interface difference $l_u'$ may be set between an interface LS3 of the gelatin 202 in the test tube 14 (corresponding to the liquid surface LS1 of the first exemplary embodiment) and the liquid surface LS2 of the liquid 36 inside the narrow tube 16.

Corresponding to the first liquid level difference $l_u$, the second liquid level difference $l_m$, and the third liquid level difference $l_b$ of the first exemplary embodiment, a difference in position in the axial direction of the narrow tube 16 between the interface LS3 of the gelatin 202 and the liquid surface LS2 inside the narrow tube 16 is the first interface difference $l_u'$, a difference in position in the axial direction of the narrow tube 16 between the liquid surface LS2 inside the narrow tube 16 and the bottom end face (on the basal face side of the test tube 14) of the narrow tube 16 is a second interface difference $l_m'$, and a difference in position in the axial direction of the narrow tube 16 between the basal face of the test tube 14 and the bottom end face of the narrow tube 16 is a third interface difference $l_b'$ (see FIG. 16).

Note that the gelatin 202 employed is employed with a water content by mass of 95%.

The narrow tube 16 has one end inserted into the test tube 14 and the other end open to the atmosphere. Namely, due to the coagulated gelatin 202 being disposed inside the test tube 14, there is no need for a syringe pump 20 or the like in order to induce the first interface difference $l_u'$ between the liquid surface LS1 and the liquid surface LS2, as was the case in the first exemplary embodiment. Moreover, a pipe 206 to feed the liquid 36 from the liquid feed device 204 is in communication with a position where the liquid 36 is disposed in the narrow tube 16.

Note that in FIG. 16, the discharge direction of the liquid jet MJ (the open end of the narrow tube 16) is vertically upward; however, there is no limitation thereto. Namely, application may also be made to cases in which the discharge direction is a horizontal direction or vertically downward.

Operation of the liquid jet discharge device 200 will now be described.

The liquid jet discharge device 200 is, similarly to the liquid jet discharge device 10 according to the first exemplary embodiment, capable of discharging a long, thin liquid jet MJ at high velocity increase ratio β from the liquid surface LS2 inside the narrow tube 16.

In particular, in the liquid jet discharge device 200, the water content of the gelatin 202 disposed inside the test tube 14 is 95%, and so there is a small difference between the acoustic impedance of the gelatin 202 and the acoustic impedance of the liquid 36. Thus, a fall in the energy transmission rate at the interface between the gelatin 202 in the test tube 14 and the liquid 36 in the narrow tube 16 is suppressed, enabling good discharge of the liquid jet MJ.

Although the gelatin 202 employed most preferably has the same acoustic impedance as that of the liquid 36, there may be a slight difference thereto. Confirmation was made that the liquid jet MJ is discharged from the liquid jet discharge device 200 at least until the acoustic impedance of the gelatin 202 is about 1.5 times the acoustic impedance of the liquid 36.

Note that an acoustic impedance Z is expressed as $Z=\rho c$, wherein $\rho$ is the density of a medium, in this case the gelatin 202, and c is the speed of sound in the medium. Thus, in the present exemplary embodiment, the acoustic impedance is computed from catalogue values of the density and speed of sound of the gelatin 202.

Moreover, in the liquid jet discharge device 200, due to disposing the coagulated gelatin 202 in the test tube 14, the liquid 36 is prevented from flowing out from the test tube 14 even in cases in which the discharge direction of microjets is a horizontal direction or direction vertically downward. Furthermore, due to the narrow tube 16 being sufficiently narrow, the liquid surface LS2 is maintained due to the surface tension of the liquid 36, preventing liquid from flowing out from the narrow tube 16. There is accordingly no limitation to the installation direction of the liquid jet discharge device 200, and the liquid jet MJ may be discharged in any direction (for example, in a horizontal direction or vertically downward).

Note that in cases in which the liquid 36 is disposed in the test tube 14, it is thought that the liquid surface LS1 is maintained by the surface tension of the liquid 36 as long as the difference between the inner diameter of the test tube 14 and the outer diameter of the narrow tube 16 is sufficiently small. However, there is a concern that the velocity increase ratio β of the liquid jet MJ will become small due the effect from the tube walls of the test tube 14 on the liquid 36 (energy loss due to viscous dissipation) becoming larger, and the pressure impulse gradient of the liquid 36 inside the test tube 14 becoming smaller. In contrast thereto, in the liquid jet discharge device 200, due to the gelatin 202 inside the test tube 14 being coagulated, there is no concern that the liquid 36 might flow out from the test tube 14 even if the difference between the inner diameter of the test tube 14 and the outer diameter of the narrow tube 16 is made sufficiently large. The pressure impulse gradient in the gelatin 202 inside the test tube 14 may accordingly be made sufficiently large, enabling good discharge of the liquid jet MJ at high velocity increase ratio β.

Furthermore, due to the gelatin 202 being coagulated, the position of the interface LS3 of the gelatin 202 inside the test tube 14 is fixed, and so the first interface difference $l_u'$ may be set by setting only the position of the liquid surface LS2 of the liquid 36 inside the narrow tube 16. Namely, the first interface difference $l_u'$ may be set by controlling only the amount of liquid fed from the liquid feed device 204 into the narrow tube 16. A mechanism to supply a negative pressure or a positive pressure to the narrow tube 16 and the test tube 14 is accordingly not required, further simplifying the configuration of the liquid jet discharge device 200.

Moreover, accompanying this, the end portion of the narrow tube 16 on the opposite side to the test tube 14 side is open to the atmosphere, facilitating placement of the discharge target.

Furthermore, in the liquid jet discharge device 200, the liquid 36 to be discharged as the liquid jet MJ need only be disposed inside the narrow tube 16 since the gelatin 202 is disposed in the test tube 14. Namely, the amount of the liquid 36 needed to discharge the liquid jet MJ may be reduced. The advantage of being able to reduce the amount of liquid 36 used is particularly large in cases in which a high cost liquid 36 or the like is discharged.

Moreover, when replacing the liquid 36 being used in the liquid jet discharge device 200, due to the liquid 36 only being disposed inside the narrow tube 16, a different liquid may simply be fed into the narrow tube 16 after the liquid 36 inside the narrow tube 16 has been expelled. Namely, there is no need to replace the gelatin 202 disposed inside the test tube 14, and so there is the advantage that a small amount of replacement liquid suffices.

Note that although in the present exemplary embodiment, an example has been described in which the gelatin 202 is disposed in the test tube 14, there is no limitation thereto. Any solid body, namely any non-fluid substance, that has an acoustic impedance satisfying the conditions given above with respect to the acoustic impedance of the liquid 36 is applicable in the present exemplary embodiment. For example, polydimethylsiloxane (PDMS) may be applicable.

Moreover, although in the liquid jet discharge device 200, the gelatin 202 is disposed in the whole of the test tube 14, from the perspective of preventing the liquid 36 from flowing out irrespective of the discharge direction of the liquid jet MJ, a configuration may be adopted to prevent the liquid 36 from flowing out by, for example, forming a layer of the gelatin 202 only in the vicinity of the interface LS3. Or, another conceivable configuration is one that suppresses the liquid 36 from flowing out by providing a lid at a position of the liquid surface LS1 of the test tube 14 (see FIG. 1).

Moreover, from the perspective of suppressing the amount of the liquid 36 used to discharge the liquid jet MJ in the liquid jet discharge device 200, a liquid that is different to the liquid 36 inside the narrow tube 16 may conceivably be disposed inside the test tube 14 (at the outside the narrow tube 16).

In such cases, the different liquid needs to be a liquid that does not mix with the liquid 36, and does not cause a chemical reaction with the liquid 36.

Further, there is a need to make the difference between the inner diameter of the test tube 14 and the outer diameter of the narrow tube 16 sufficiently small in order that liquid does not flow out from the test tube 14 when the discharge direction of the liquid jet MJ is vertically downward (so as to enable flow to be prevented by the surface tension of the liquid).

Moreover, in order to set the first interface difference $l_u'$, there is a need to cause a pressure difference to act on the test tube 14 and the narrow tube 16. When configured in such a manner, different liquids may be discharged by replacing only the liquid 36.

Fourth Exemplary Embodiment

A liquid jet discharge device according to a fourth exemplary embodiment of the present invention will be described, with reference to FIG. 19. The same reference numerals are appended to similar components to those of the second and third exemplary embodiments, and description thereof will be omitted. Only the points differing from the third exemplary embodiment will be described.

Figure 19:
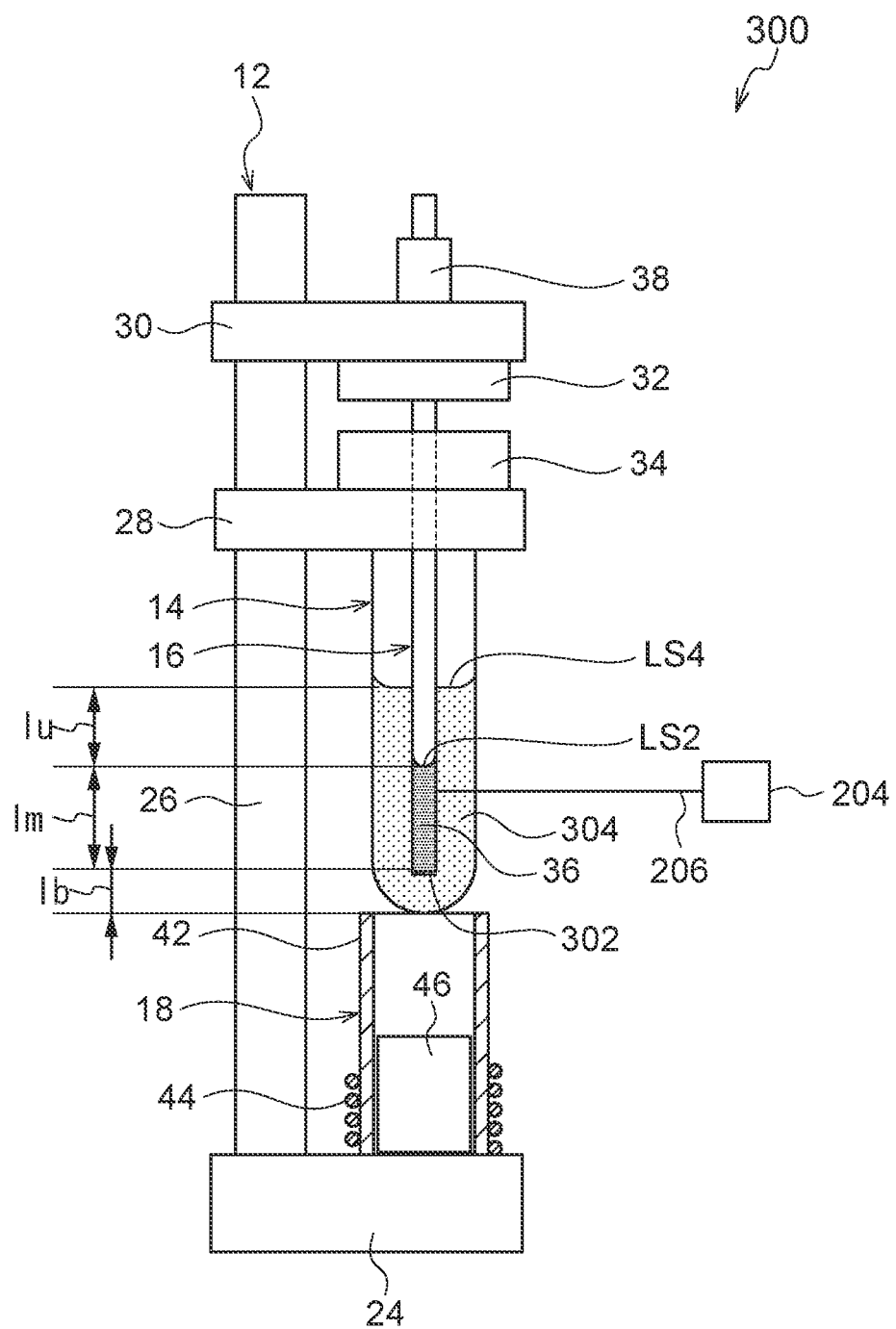
FIG. 19 is a schematic configuration diagram of a liquid jet discharge device according to a fourth exemplary embodiment.

As illustrated in FIG. 19, a liquid jet discharge device 300 is configured including a membrane 302 at the bottom end of the narrow tube 16. The interior of the test tube 14 is thereby separated into the interior of the narrow tube 16 and the exterior of the narrow tube 16.

Thus, the liquid 36 to discharge the liquid jet is disposed inside the narrow tube 16, and a liquid 304 that is different to the liquid 36 (for example, water) is disposed inside the test tube 14 but outside the narrow tube 16. The membrane 302 and the liquid 304 correspond respectively to a membrane and a transmission liquid, which are examples of a transmission medium of the present disclosure.

Specifically, the liquid 36 is fed into the narrow tube 16 from a liquid feed device 204. This enables the first liquid level difference $l_u$ between a liquid surface LS4 of the liquid 304 in the test tube 14 (corresponding to the liquid surface LS1 of the first exemplary embodiment) and the liquid surface LS2 of the liquid 36 inside the narrow tube 16 to be set by controlling the amount of the liquid 36 fed into the narrow tube 16 from the liquid feed device 204.

Note that gelatin employed as the membrane 302 has a water content of 95% by mass.

Moreover, although in FIG. 19 the discharge direction of the liquid jet MJ (the open end of the narrow tube 16) is vertically upward, there is no limitation thereto. Namely, application may be made to cases in which the discharge direction is a horizontal direction or vertically downward.

Operation of the liquid jet discharge device 300 will now be described.

Similarly to the liquid jet discharge device 10 according to the second exemplary embodiment, the liquid jet discharge device 300 is capable of discharging a long, thin liquid jet MJ at high velocity increase ratio β from the liquid surface LS2 inside the narrow tube 16.

In particular, in the liquid jet discharge device 300, due to the liquid 36 and the liquid 304 being separated from each other by the membrane 302 formed at the bottom end of the narrow tube 16, the membrane 302 deforms due to a pressure wave from the liquid 304 propagating to the membrane 302, thereby efficiently propagating the pressure wave to the liquids 36. Namely, the energy transmission rate is suppressed from falling at the interface between the liquid 304 and the membrane 302 inside the test tube 14 and at the interface between the membrane 302 and the liquid 36 inside the narrow tube 16, enabling good discharge of the liquid jet MJ.

Note that the membrane 302 is not limited to any particular material.

Moreover, due to the position of the membrane 302 formed at the bottom end of the narrow tube 16 being fixed, by fixing the amount of the liquid 304 disposed inside the test tube 14 and outside the narrow tube 16, the first interface difference $l_u$ may be set by setting only the position of the liquid surface LS2 of the liquid 36 inside the narrow tube 16. Namely, the first interface difference $l_u$ may be set by controlling only the amount of the liquid 36 fed from the liquid feed device 204 into the narrow tube 16. A mechanism to supply a negative pressure or a positive pressure to the narrow tube 16 and the test tube 14 is accordingly not required, further simplifying the configuration of the liquid jet discharge device 300.

Moreover, accompanying this, the end portion of the narrow tube 16 on the opposite side to the test tube 14 side is open to the atmosphere, facilitating placement of the discharge target.

Moreover, in the liquid jet discharge device 300, due to the membrane 302 being formed at the bottom end of the narrow tube 16, the liquid 36 to discharge the liquid jet MJ need only be disposed inside the narrow tube 16. Namely, the amount of the liquid 36 needed to discharge the liquid jet MJ may be reduced. The advantage of being able to reduce the amount of liquid 36 used is particularly large in cases in which a high cost liquid 36 or the like is discharged.

Moreover, when replacing the liquid 36 being used in the liquid jet discharge device 300, due to the liquid 36 only being disposed inside the narrow tube 16, a different liquid may simply be fed into the narrow tube 16 after the liquid 36 inside the narrow tube 16 has been expelled. Namely, there is no need to replace the liquid 304 disposed inside the test tube 14, and so there is the advantage that a small amount of replacement liquid suffices.

Moreover, in the liquid jet discharge device 300, due to employing the liquid 304 as an example of a transmission medium in the test tube 14 outside the narrow tube 16, there is the advantage of it being easy to dispose the transmission medium of the test tube 14 outside the narrow tube 16, irrespective of the shape of the container, such as the test tube 14.

Note that although in the present exemplary embodiment an example has been described in which the membrane 302 is formed at the bottom end of the narrow tube 16, the membrane 302 may be formed inside the narrow tube 16.

Fifth Exemplary Embodiment

Figure 20:
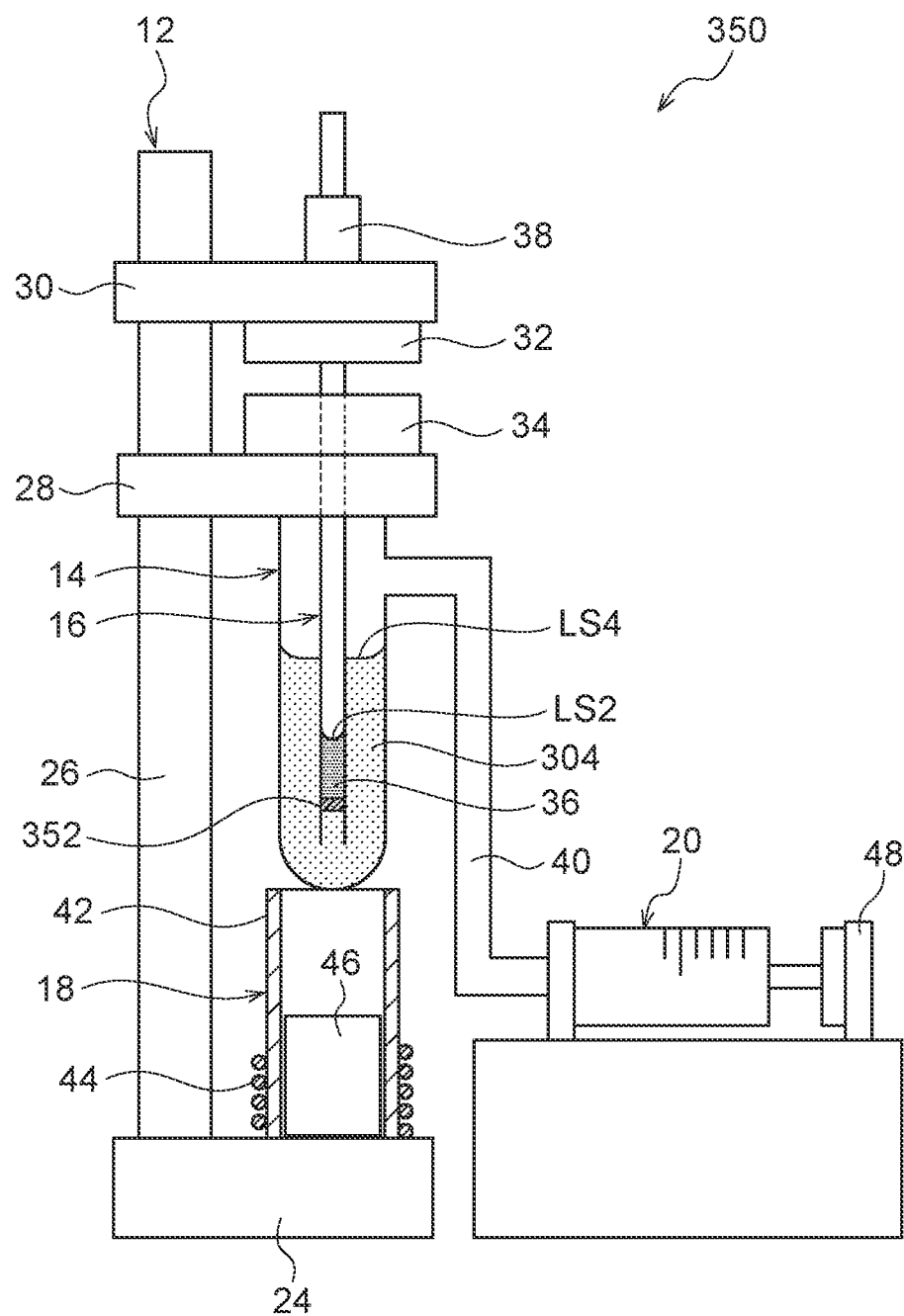
FIG. 20 is a schematic configuration diagram of a liquid jet discharge device according to a fifth exemplary embodiment.

A liquid jet discharge device according to a fifth exemplary embodiment of the present invention will be described, with reference to FIG. 20. The same reference numerals are appended to similar components to those of the second and fourth exemplary embodiments, and description thereof will be omitted. Only the points differing from the second exemplary embodiment and the fourth exemplary embodiment will be described.

A liquid jet discharge device 350 has substantially the same configuration as that of the liquid jet discharge device 100 of the second exemplary embodiment, but differs in the point that a plug 352 formed from gelatin is disposed inside a narrow tube 16. In a test tube 14, the narrow tube 16 is thereby separated by the plug 352 into a side opposite to the base of the test tube 14, and a side of the base of the test tube 14. Thus, a liquid 36 to be discharged is disposed in the narrow tube 16 on the opposite side of the plug 352 to the base of the test tube 14, and a liquid 304 differing from the liquid 36 is disposed in the narrow tube 16 on the test tube 14 base side of the plug 352, and also inside the test tube 14 and outside the narrow tube 16.

Note that the gelatin employed for the plug 352 has a water content of 95% by mass. Moreover, the plug 352 is able to move up or down along an axial direction inside the narrow tube 16, while still separating the liquid 36 and the liquid 304.

Operation of the liquid jet discharge device 350 will now be described.

Similarly to the liquid jet discharge device 10 according to the second exemplary embodiment, the liquid jet discharge device 350 is capable of discharging a long, thin liquid jet MJ at high velocity increase ratio β from the liquid surface LS2 inside the narrow tube 16.

In particular, in the liquid jet discharge device 350, due to the gelatin configuring the plug 352 disposed inside the narrow tube 16 having a water content of 95%, there is little difference between the acoustic impedance of the plug 352 and the acoustic impedances of the liquids 36, 304. The energy transmission rate is accordingly suppressed from falling at the interface between the liquid 304 inside the test tube 14 and the plug 352, and at the interface between the plug 352 and the liquid 36 inside the narrow tube 16, enabling good discharge of the liquid jet MJ.

Note that although the gelatin employed in the plug 352 most preferably has the same acoustic impedance as that of the liquids 36, 304, there may be a slight difference therebetween. Confirmation was made that the liquid jet MJ is discharged from the liquid jet discharge device 350 at least until the acoustic impedance of the gelatin is about 1.5 times the acoustic impedance of the liquids 36, 304.

Moreover, the plug 352 disposed inside the narrow tube 16 is able to move along the axial direction of the narrow tube 16. Thus the first interface difference $l_u$ may be set by increasing or reducing the pressure of the gas portion of the outside of the narrow tube 16 in the test tube 14 by driving the syringe pump 20, such that the liquid surface LS2 of the liquid 36 inside the narrow tube 16 and the liquid surface LS4 of the liquid 304 in the test tube 14 and outside the narrow tube 16 are moved in opposite directions to each other. Namely, the first interface difference $l_u$ between the liquid surface LS2 of the liquid 36 and the liquid surface LS4 of the liquid 304, the liquid 36 and the liquid 304 being different liquids, may be set by driving only the syringe pump 20. The configuration of the liquid jet discharge device 350 is accordingly simplified.

Furthermore, accompanying this, the end portion of the narrow tube 16 on the opposite side to the test tube 14 side is open to the atmosphere, facilitating placement of the discharge target.

Moreover, in the liquid jet discharge device 350, due to the plug 352 being disposed inside the narrow tube 16, the liquid 36 to be discharged as the liquid jet MJ need only be disposed inside the narrow tube 16 on the opposite side of the plug 352 to the base of the test tube 14. Namely, the amount of the liquid 36 needed to discharge the liquid jet MJ may be reduced. The advantage of being able to reduce the amount of liquid 36 used is particularly large in cases in which a high cost liquid 36 or the like is discharged.

Moreover, to replace the liquid 36 being used in the liquid jet discharge device 350, due to the liquid 36 only being disposed inside the narrow tube 16, a different liquid may simply be fed into the narrow tube 16 after the liquid 36 inside the narrow tube 16 has been expelled. Namely, there is no need to replace the liquid 304 disposed inside the test tube 14, and so there is the advantage that a small amount of replacement liquid suffices.

Moreover, in the liquid jet discharge device 350, due to employing the liquid 304 as a pressure wave transmission medium in the test tube 14 and outside the narrow tube 16, there is an advantage that the transmission medium is easily disposed in the test tube 14 and outside the narrow tube 16 irrespective of the shape of the container such as the test tube 14.

Note that although in the present exemplary embodiment an example has been described in which the plug 352 formed from gelatin is formed inside the tube 16, there is no limitation thereto. Any solid body, namely any non-fluid substance, that has an acoustic impedance satisfying the conditions given above with respect to the acoustic impedance of the liquid 36 is applicable in the present exemplary embodiment. For example, polydimethylsiloxane (PDMS) may be applicable.

Sixth Exemplary Embodiment

A liquid jet discharge device according to a sixth exemplary embodiment of the present invention will be described, with reference to FIG. 21. The same reference numerals are appended to similar components to those of the second exemplary embodiment, and description thereof will be omitted. Only the points differing from the second exemplary embodiment will be described.

Figure 21:
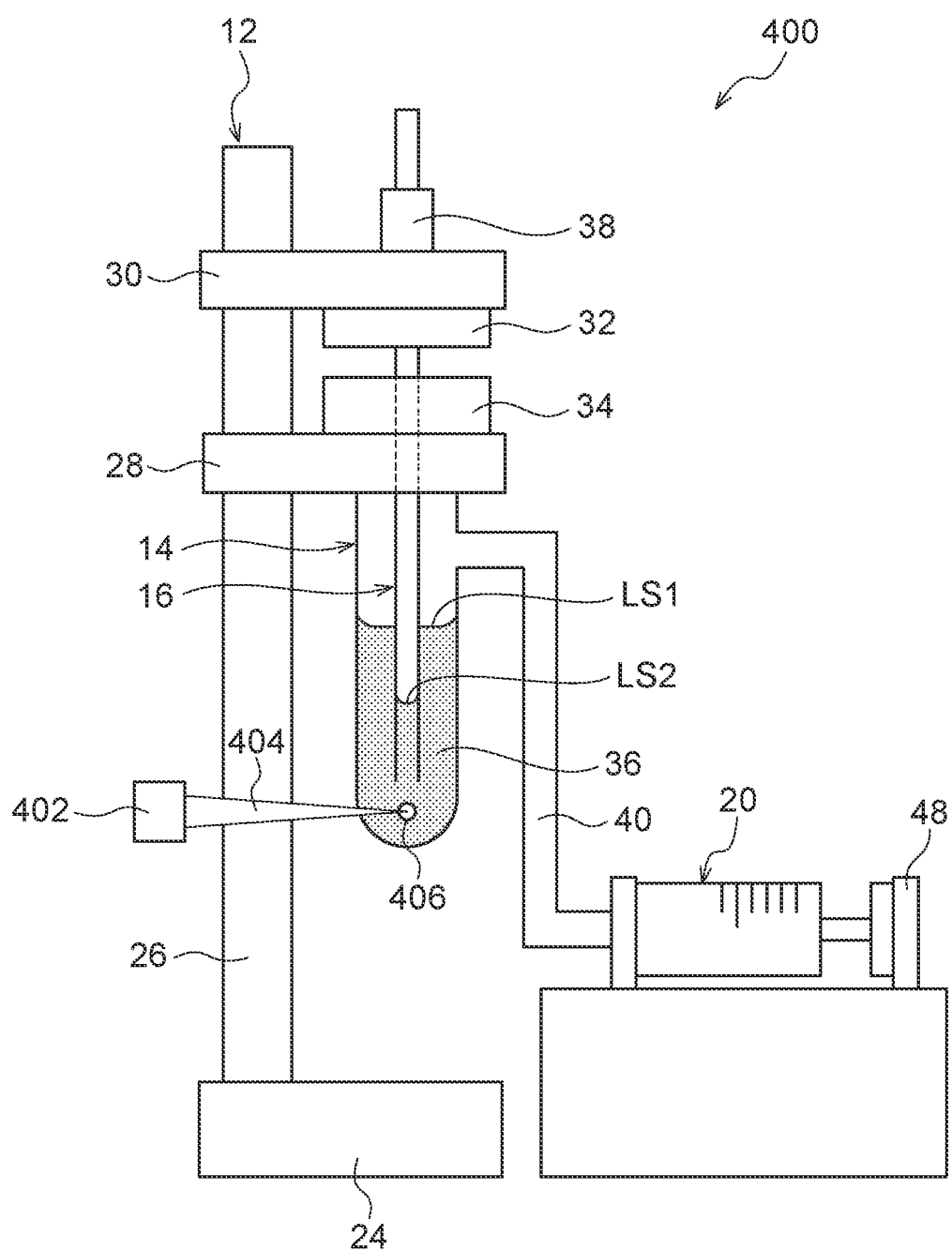
FIG. 21 is a schematic configuration diagram of a liquid jet discharge device according to a sixth exemplary embodiment.

As illustrated in FIG. 21, instead of the coilgun 18, which is an example of an impulse force imparting mechanism serving as a generation mechanism in the liquid jet discharge device 100 of the second exemplary embodiment, the liquid jet discharge device 400 includes a pulse laser emitting device 402, this being an example of a laser emitting mechanism, disposed at the side of a base of a test tube 14. The pulse laser emitting device 402 is a device that has a built-in light-focusing lens, and that emits a pulse laser focused below the narrow tube 16 inside the test tube 14.

The operation of the liquid jet discharge device 400 will now be described.

As illustrated in FIG. 21, in the liquid jet discharge device 400, a liquid 36 is poured into the test tube 14, and a syringe pump 20 is operated to set a predetermined liquid level difference between a first liquid surface LS1 and a second liquid surface LS2. In this state, a pulse laser 404 is emitted from the pulse laser emitting device 402 toward the test tube 14.

The pulse laser 404 generates bubbles 406 within the liquid 36 due to being focused below the narrow tube 16 inside the test tube 14. A pressure wave that arises in the liquid 36 due to the generation of the bubbles 406 propagates within the narrow tube 16, and a liquid jet MJ is discharged from the liquid surface LS2.

In this manner, since the liquid jet discharge device 400 simply needs to emit the pulse laser 404 focused on the test tube 14 in order to generate the pressure wave in the liquid 36, there is no need to move the test tube 14 each time a pressure wave is generated, with the advantage that the device is stable.

Seventh Exemplary Embodiment

A liquid jet discharge device according to a seventh exemplary embodiment of the present invention will be described, with reference to FIG. 22. The same reference numerals are appended to similar components to those of the second exemplary embodiment, and description thereof will be omitted. Only the points differing from the second exemplary embodiment will be described.

Figure 22:
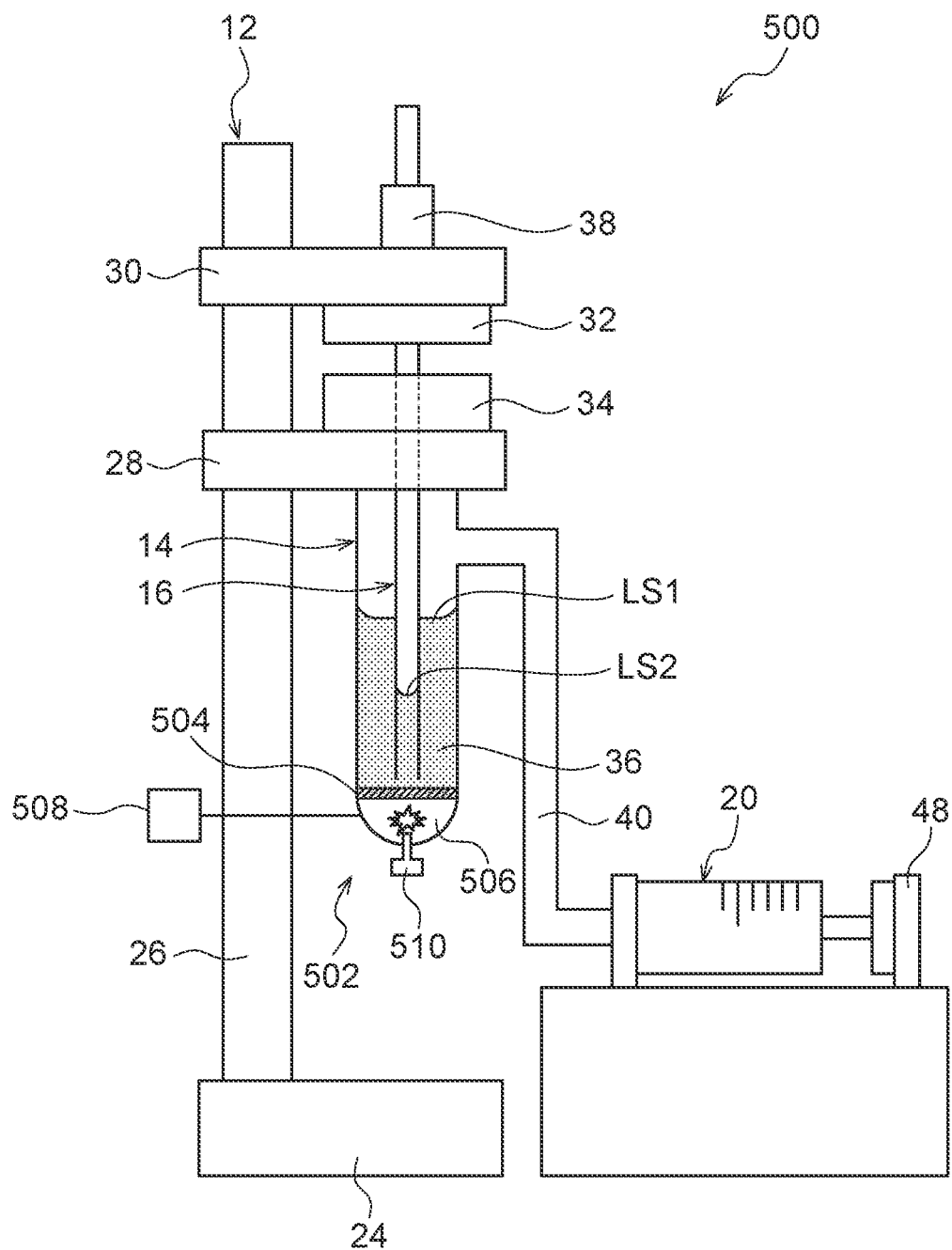
FIG. 22 is a schematic configuration diagram of a liquid jet discharge device according to a seventh exemplary embodiment.

As illustrated in FIG. 22, instead of the coilgun 18, which is an example of an impulse force imparting mechanism serving as a generation mechanism in the liquid jet discharge device 100 of the second exemplary embodiment, a liquid jet discharge device 500 is provided with an explosive device 502, this being an example of an explosive mechanism.

The explosive device 502 includes an explosion chamber 506, partitioned off at a base of a test tube 14 by a membrane 504 formed from gelatin at the bottom of the narrow tube 16. The explosive device 502 further includes an explosive feed device 508 that is in communication with the explosion chamber 506 and that feeds a powdered explosive into the explosion chamber 506, a detonator 510 to ignite the explosive provided to the explosion chamber 506, and a non-illustrated exhaust gas hole provided to the explosion chamber 506.

The operation of the liquid jet discharge device 500 will now be described.

As illustrated in FIG. 22, in the liquid jet discharge device 500, a liquid 36 is poured into the test tube 14, and a syringe pump 20 is operated to set a predetermined liquid level difference between a first liquid surface LS1 and a second liquid surface LS2. In this state, a predetermined amount of the powdered explosive is fed from the explosive feed device 508 into the explosion chamber 506, and an explosion is generated in the explosion chamber 506 by driving the detonator 510. A shock wave due to this explosion propagates through the membrane 504 to the liquid 36, and a liquid jet MJ is discharged from the liquid surface LS2 of the liquid 36 in the narrow tube 16.

In this manner, since the liquid jet discharge device 500 simply needs to ignite the explosive in the explosion chamber 506 at the base of the test tube 14 in order to generate a pressure wave in the liquid 36, there is no need to move the test tube 14 each time a pressure wave is generated, with the advantage that the device is stable.

Eighth Exemplary Embodiment

A liquid jet discharge device according to an eighth exemplary embodiment of the present invention will be described, with reference to FIG. 23. The same reference numerals are appended to similar components to those of the second exemplary embodiment, and description thereof will be omitted. Only the points differing from the second exemplary embodiment will be described.

Figure 23:
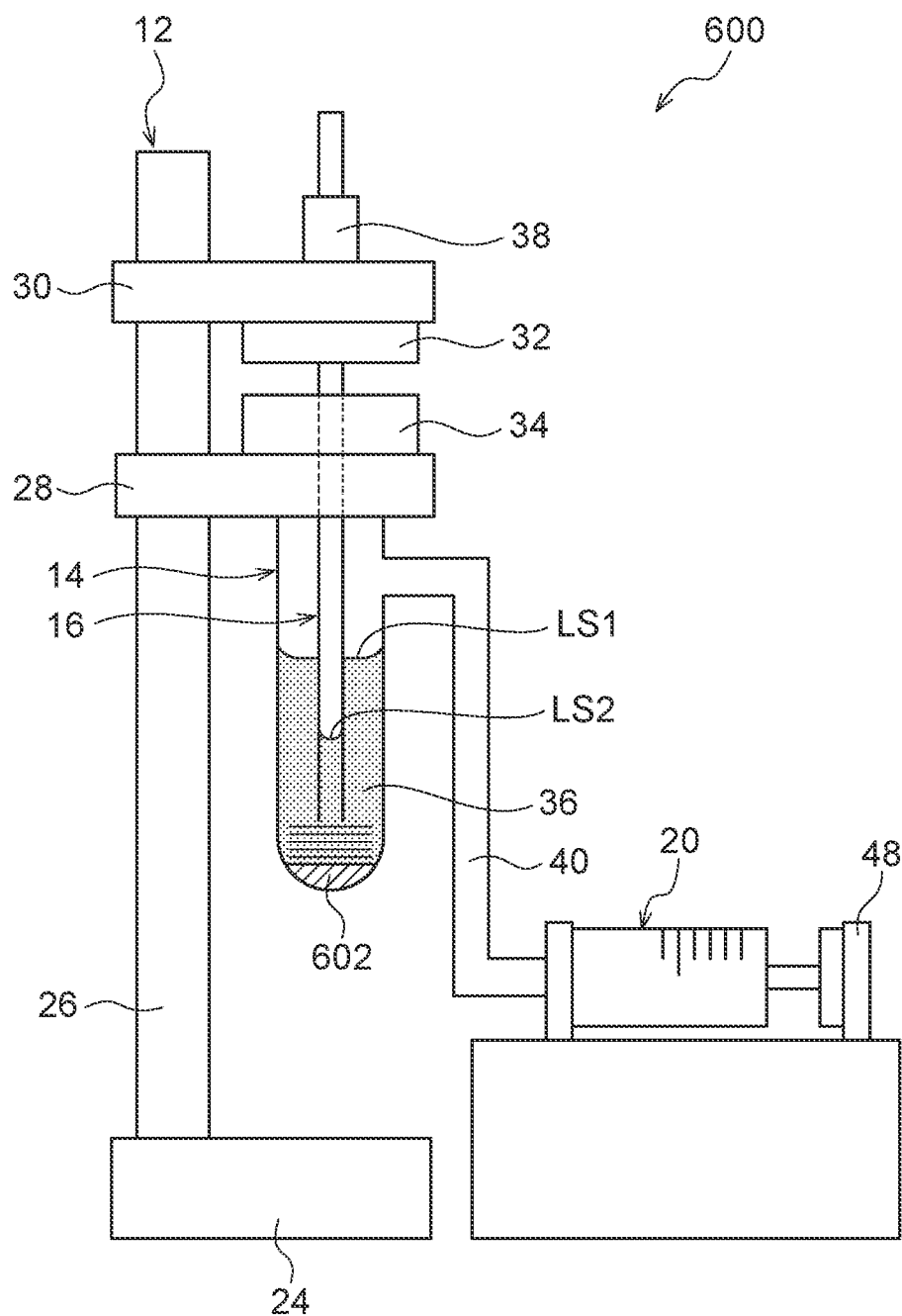
FIG. 23 is a schematic configuration diagram of a liquid jet discharge device according to an eighth exemplary embodiment.

As illustrated in FIG. 23, instead of the coilgun 18, which is an example of an impulse force imparting mechanism serving as a generation mechanism in the liquid jet discharge device 100 of the second exemplary embodiment, a liquid jet discharge device 600 is provided with an ultrasonic wave generation device 602, this being an example of an ultrasonic wave imparting mechanism.

The ultrasonic wave generation device 602 is disposed at the base side of the test tube 14, and emits an ultrasonic wave toward the bottom end portion side of the narrow tube 16.

Operation of the liquid jet discharge device 600 will now be described.

As illustrated in FIG. 23, in the liquid jet discharge device 600, a liquid 36 is poured into the test tube 14, and in a state in which a predetermined liquid level difference is set between a first liquid surface LS1 and a second liquid surface LS2, the ultrasonic wave generation device 602 is driven, and an ultrasonic wave is emitted toward the bottom end portion of the narrow tube 16. The ultrasonic wave propagates through the liquid 36 in the narrow tube 16 and is focused at the liquid surface LS2. As a result, a liquid jet MJ is discharged from the liquid surface LS2.

In this manner, since the liquid jet discharge device 600 simply needs to emit an ultrasonic wave in the liquid 36, there is no need to move the test tube 14 each time a pressure wave is generated, with the advantage that the device is stable.

Other Embodiments

Although liquid jet discharge devices according to the first to the eighth exemplary embodiments have been described, the present invention is not limited thereto.

For example, although the first to the fifth exemplary embodiments have been described in which the coilgun 18 is employed as an example of an impulse force imparting mechanism, there is no limitation to a coilgun 18, and the impulse force imparting mechanism may be any mechanism capable of imparting impulse force by a strike to a container, in this case the test tube 14. For example, conceivably an impulse force by a strike to the test tube 14 may be caused by letting the test tube 14 free fall.

Moreover, although the first exemplary embodiment to the fifth exemplary embodiment have been disclosed in which the impulse force imparting mechanism is employed as a generation mechanism, the impulse force imparting mechanism may be replaced by the laser emitting mechanism, the explosive mechanism, or the ultrasonic wave imparting mechanism indicated in the examples of the sixth exemplary embodiment to the eighth exemplary embodiment. However, in cases in which the impulse force imparting mechanism is replaced by the laser emitting mechanism, the transmission medium disposed outside the narrow tube 16 and inside the test tube 14, which is a container, needs to be a liquid, so this is only applicable to the first, second, fourth, and fifth exemplary embodiments.

Although the first, second, and fifth to eighth exemplary embodiments have been disclosed in which the syringe pump 20, this being an example of a narrow tube internal liquid surface displacement mechanism or a narrow tube external interface displacement mechanism to increase or reduce the pressure of the gas portion inside the narrow tube 16 or the gas portion outside the narrow tube 16, is employed as an adjustment mechanism, there is no limitation to the syringe pump 20. Any mechanism capable of inducing a first liquid level difference $l_u$ between the liquid surface LS1, LS4 (interface LS3) outside the narrow tube 16 and the liquid surface LS2 inside the narrow tube 16 may be employed therefor. For example, conceivably the first liquid level difference $l_u$ may be induced between the liquid surface LS1, LS4 outside the narrow tube 16 and the liquid surface LS2 inside the narrow tube 16 by reducing the pressure of the gas portion outside the narrow tube 16 by closing off the portion of the test tube 14 outside the narrow tube 16 using a rubber plug or the like, and inserting an injection needle through the rubber plug. Moreover, conceivably, instead of increasing or reducing the pressure of the gas portion, for example, a lid may be pressed to displace the liquid surface of the narrow tube 16 or the liquid surface of the portion of the test tube 14 outside the narrow tube 16 in the axial direction of the narrow tube 16 so as to induce the first liquid level difference $l_u$ between the liquid surface LS1, LS4 outside the narrow tube 16 and the liquid surface LS2 inside the narrow tube 16. However, it is desirable that a mechanism having excellent ease-of-operation and safety is employed therefor.

Furthermore, in the instances in which a transmission medium disposed outside the narrow tube 16 is the gelatin 202 as in the third exemplary embodiment for example, or in instances in which the membrane 302 is formed at the bottom end of the narrow tube 16 as in the fourth exemplary embodiment such that the amount of the liquid 304 outside the narrow tube 16 does not change from its initial state, a discharge liquid feed mechanism to adjust the amount of the liquid 36 fed into the narrow tube 16, for example an adjustment mechanism such as that of the liquid feed device 204, may be provided in order to maintain a fixed interface LS3 or liquid surface LS4 outside the narrow tube 16.

Although the liquid jet discharge devices in the first to the eighth exemplary embodiments have configurations in which the test tube 14 and the narrow tube 16 are disposed in a vertical orientation, and the liquid jet MJ is discharged vertically upward, there is no limitation thereto. For example, a liquid jet MJ with a high velocity increase ratio may be discharged in a horizontal direction by a configuration in which the test tube 14 and the narrow tube 16 are disposed in a horizontal orientation, such that the liquid surface LS2 inside the narrow tube 16 is further to the base side of the test tube 14 than the liquid surface LS1 outside the narrow tube 16 (i.e., the first liquid level difference $l_u$ is induced between the liquid surface LS1 and the liquid surface LS2). Note that in such cases, the liquid surfaces LS1, LS2 need to be maintained in a concave shape that dips in toward the opposite side to the base side of the test tube 14 using the action of surface tension by making the distance in the test tube 14 between the inner wall of the test tube 14 and the outer wall of the narrow tube 16, and the inner diameter d of the narrow tube 16, sufficiently small. For example, it is confirmed that when silicone oil is employed as the liquid 36, the liquid surfaces LS1, LS2 may be maintained in a concave shape that dips in toward the opposite side of the test tube 14 to the base side of the test tube 14 even when the test tube 14 is sloped away from a vertical orientation, so long as the distance between the inner wall of the test tube 14 and the outer wall of the narrow tube 16 is 500 μm or less, and the inner diameter d of the narrow tube 16 is 1 mm or less.

Moreover, although the liquid jet discharge devices according to the first to the fifth exemplary embodiments are configured such that impulse force is imparted to the base of the test tube 14, there is no limitation thereto. Namely, a configuration may be employed in which an impulse force is imparted to a side face of the test tube 14 at a position further to the base side of the test tube 14 than the liquid surface LS2 inside the narrow tube 16. However, when the impulse force imparting position is at the base side of the test tube 14, there is a high conversion efficiency to convert a fixed impulse force to an acceleration of the liquid 36 in the narrow tube 16, with the highest conversion efficiency being when the impulse force is imparted to the base of the test tube 14.

Furthermore, in the first to the fifth exemplary embodiments configuration is such that impulse force is imparted to the test tube 14 by using the metal rod 46 in order to discharge the liquid jet MJ, there is no limitation thereto. Any configuration may be adopted in which a large acceleration may be imparted to the liquid 36 inside the narrow tube 16 in a short period of time. For example, conceivably a soft object such as a rubber member or a urethane member may be smashed against the test tube 14 instead of the metal rod 46. In such cases, due to lengthening of the duration of contact between the rubber member or the like and the test tube 14, this does not fall within what is referred to as an "impulse force"; however, it is possible to discharge a liquid jet MJ from the liquid surface LS2 so long as a large acceleration (100 mm²/s or greater) is imparted to the liquid 36 inside the narrow tube 16 in a short period of time ($10^{-4}$ s or less).

Moreover, although the liquid jet discharge devices described in the first to the eighth exemplary embodiments have a single narrow tube disposed in each test tube, there may be plural narrow tubes disposed inside a single test tube. In such cases a liquid jet MJ is discharged from each of the narrow tubes by imparting an impulse force or the like to a single test tube. Namely, plural liquid jets MJ may be discharged.

In cases in which a liquid jet discharge device according to the present exemplary embodiments is applied in medical treatment by, for example, being employed as a needleless injector, a liquid jet discharge device in which the gelatin 202 is employed as a transmission medium filling the outside of the narrow tube 16, as in the third exemplary embodiment, may conceivably be combined with, for example, the type of liquid jet discharge device that employs a powdered explosive as in the sixth exemplary embodiment.

Namely, a predetermined amount of liquid medicine or the like may be disposed in inside the narrow tube 16 as the liquid 36, a first interface difference $l_u{}'$ set between the liquid surface LS2 and the interface LS3, and the powdered explosive ignited in the explosion chamber 506 such that the liquid 36, this being the liquid medicine, is discharged from the narrow tube 16. In such cases, the position to which the liquid medicine is delivered may be changed between, for example, a position on the skin surface, an intradermal position, a subcutaneous position, or an intramuscular position by adjusting the first interface difference $l_u{}'$ to adjust the velocity increase ratio β.

Moreover, due to the liquid 36, which is the liquid medicine, only being disposed within the narrow tube 16, the liquid medicine is easily changed, and the amount of liquid medicine wasted may be reduced.

Note that although the test tube 14 and the like are supported by the stand 12 in FIG. 16 and FIG. 22, when employed as a needleless injector, the test tube 14 and the like may be employed without the stand 12, and the discharge direction of the liquid jet may freely changeable to accommodate the posture of a subject receiving medical treatment.

The present disclosure provides a drug delivery method including: a first process of disposing a transmission medium at a base side of a container, and, in a narrow tube that is open at both ends disposed such that one end of the narrow tube is inserted into the transmission medium of the container and the other end of the narrow tube is disposed outside the transmission medium, disposing a liquid drug inside the narrow tube so as to enable pressure transmission from the transmission medium, the liquid drug contacting at least at an inner face of the narrow tube at a contact angle of less than 90 degrees; and a second process of, in a state in which a liquid surface of the liquid drug inside the narrow tube and an interface of the transmission medium outside the narrow tube and inside the container have been adjusted in position along an axial direction of the narrow tube, generating a pressure wave in the transmission medium inside the narrow tube such that at least part of the drug inside the narrow tube is discharged as a liquid jet toward a skin surface of a patient.

The entire disclosures of Japanese Patent Application No. 2015-099054 filed on May 14, 2015, and of Japanese Patent Application No. 20155-166119 filed on Aug. 25, 2015, are incorporated by reference in the present specification.

Supplement

A first aspect of the present disclosure provides a liquid microjet high speed discharge device including: a container having a liquid stored at a base side thereof; a narrow tube that is open at both ends, disposed such that one end thereof is inserted into the liquid of the container and the other end thereof is disposed outside the liquid of the container, the liquid contacting at least at an inner face of the narrow tube at a contact angle of less than 90 degrees; a liquid level difference forming means that causes a liquid surface inside the narrow tube to be positioned further to the base side of the container than a liquid surface inside the container and outside the narrow tube; and an acceleration imparting means that imparts an acceleration to the liquid inside the narrow tube such that a liquid microjet is discharged from the liquid inside the narrow tube.

Moreover, a second aspect of the present disclosure provides the liquid microjet high speed discharge device of the first aspect of the present disclosure, wherein the acceleration imparting means is an impulse force imparting means that imparts an impulse force to the container at a position further to the container base side than the liquid surface inside the narrow tube.

Moreover, a third aspect of the present disclosure provides the liquid microjet high speed discharge device of the first aspect or the second aspect of the present disclosure, wherein the liquid level difference forming means is a pressurizing means that pressurizes a gas portion inside the narrow tube.

Moreover, a fourth aspect of the present disclosure provides the liquid microjet high speed discharge device of the first aspect or the second aspect of the present disclosure, wherein the liquid level difference forming means is a pressure reduction means that reduces the pressure of a gas portion inside the container and outside the narrow tube.

The invention claimed is:

1. A liquid jet discharge device comprising:
a narrow tube having a tube shaped body that is open at both ends, wherein a discharge liquid is disposed within the narrow tube, and wherein the discharge liquid contacts at least at an inner face of the narrow tube at a contact angle of less than 90 degrees;
a container, wherein a transmission medium is disposed within the container, wherein one end of the narrow tube contacts the transmission medium within the container so as to allow pressure to be transmitted from the transmission medium to the discharge liquid in the narrow tube;
an adjustment mechanism fluidically coupled to the container or the narrow tube and configured to increase or reduce a pressure of a gas portion inside the container or the narrow tube in order to cause a liquid surface of the discharge liquid inside the narrow tube and an interface of the transmission medium outside the narrow tube and inside the container to be staggered in position along an axial direction of the narrow tube; and
a generation mechanism configured to generate a pressure wave in the transmission medium in the container in order to propagate the pressure wave to the discharge liquid in the narrow tube and cause a liquid jet to be discharged from the liquid surface of the discharge liquid inside the narrow tube.

2. The liquid jet discharge device of claim 1, wherein the transmission medium comprises:
a transmission liquid that is disposed at least at an outside of the narrow tube and between the narrow tube and a base of the container; and
a separator member disposed between the discharge liquid in the narrow tube and the transmission liquid, where the separator member is either inside the narrow tube or at an end portion of the narrow tube so as to separate the transmission medium and the discharge liquid and to propagate a pressure wave from the transmission liquid to the discharge liquid.

3. The liquid jet discharge device of claim 2, wherein the separator member is a membrane formed either inside the narrow tube or at the end portion of the narrow tube.

4. The liquid jet discharge device of claim 3, wherein the adjustment mechanism is a liquid feed device fluidically coupled to the narrow tube and configured to feed additional discharge liquid to the narrow tube.

5. The liquid jet discharge device of claim 2, wherein the separator member is a plug disposed inside the narrow tube so as to be capable of displacement, the plug having an acoustic impedance of from 1 time to 1.5 times the acoustic impedance of the discharge liquid.

6. The liquid jet discharge device of claim 5, wherein the adjustment mechanism is a syringe pump configured to displace the liquid surface of the discharge liquid inside the narrow tube along the axial direction of the narrow tube.

7. The liquid jet discharge device of claim 5, wherein the adjustment mechanism is a syringe pump configured to displace the interface of the transmission medium outside the narrow tube and inside the container along the axial direction of the narrow tube.

8. The liquid jet discharge device of claim 2, wherein the generation mechanism is a pulse laser configured to emit a laser beam into the transmission medium at the container base.

9. The liquid jet discharge device of claim 1, wherein the transmission medium is the discharge liquid.

10. The liquid jet discharge device of claim 1, wherein the transmission medium is a solid body having an acoustic impedance of from 1 time to 1.5 times the acoustic impedance of the discharge liquid.

11. The liquid jet discharge device of claim 1, wherein the generation mechanism is coilgun coupled to the container and configured to cause an impulse at a base of the container.

12. The liquid jet discharge device of claim 1, wherein the generation mechanism is an explosive device comprising an explosion chamber containing an explosive material, wherein the explosive chamber is coupled to the container, and wherein the explosive device is configured to ignite the explosive material in the explosion chamber in order to cause an explosion to act on the transmission medium at a base of the container.

13. The liquid jet discharge device of claim 1, wherein the generation mechanism is an ultrasonic wave generating device coupled to the container and configured to generate an ultrasonic wave to act on the transmission medium at a base of the container.

14. The liquid jet discharge device of claim 1, wherein the adjustment mechanism is configured to increase or reduce pressure of the gas portion inside the container or the narrow tube so that the liquid surface of the discharge liquid inside the narrow tube is positioned further from a base of the container than the interface of the transmission medium outside the narrow tube and inside the container.

15. A liquid jet discharge method comprising:
a first process of disposing a transmission medium at a base of a container, and disposing a discharge liquid inside a narrow tube so as to enable pressure transmission from the transmission medium, the narrow tube being open at both ends and disposed such that one end thereof is inserted into the transmission medium of the container and the other end thereof is disposed outside the transmission medium, the discharge liquid contacting at least at an inner face of the narrow tube at a contact angle of less than 90 degrees; and
a second process of generating a pressure wave in the transmission medium inside the container so as to discharge a liquid jet from the discharge liquid inside the narrow tube, in a state in which a liquid surface of the discharge liquid inside the narrow tube and an interface of the transmission medium outside the narrow tube and inside the container are staggered in position along an axial direction of the narrow tube.

* * * * *